(12) United States Patent
Shimomura et al.

(10) Patent No.: US 9,195,304 B2
(45) Date of Patent: Nov. 24, 2015

(54) IMAGE PROCESSING DEVICE, IMAGE PROCESSING METHOD, AND PROGRAM

(71) Applicant: Sony Corporation, Tokyo (JP)

(72) Inventors: Hideki Shimomura, Kanagawa (JP); Takayuki Yoshigahara, Tokyo (JP); Yoshihiro Wakita, Tokyo (JP); Seiji Kobayashi, Tokyo (JP)

(73) Assignee: Sony Corporation (JP)

( * ) Notice: Subject to any disclaimer, the term of this patent is extended or adjusted under 35 U.S.C. 154(b) by 165 days.

(21) Appl. No.: 13/669,696

(22) Filed: Nov. 6, 2012

(65) Prior Publication Data

US 2013/0120445 A1    May 16, 2013

(30) Foreign Application Priority Data

Nov. 15, 2011    (JP) .................. 2011-249751

(51) Int. Cl.

| | | |
|---|---|---|
| G09G 5/00 | (2006.01) | |
| G06F 3/01 | (2006.01) | |
| G06F 19/00 | (2011.01) | |
| G06K 9/00 | (2006.01) | |
| G02B 27/01 | (2006.01) | |
| G06T 11/00 | (2006.01) | |
| G06T 11/60 | (2006.01) | |
| G06F 3/03 | (2006.01) | |
| A63F 9/24 | (2006.01) | |
| A63F 9/00 | (2006.01) | |

(52) U.S. Cl.
CPC .............. *G06F 3/011* (2013.01); *G02B 27/017* (2013.01); *G06F 3/017* (2013.01); *G06F 3/0304* (2013.01); *G06F 19/3481* (2013.01); *G06K 9/00342* (2013.01); *G06T 11/00* (2013.01); *G06T 11/60* (2013.01); *A63F 2009/0039* (2013.01); *A63F 2009/2435* (2013.01)

(58) Field of Classification Search
CPC ........................................................ G06F 3/011
USPC ................................ 482/8; 600/595; 434/257
See application file for complete search history.

(56) References Cited

U.S. PATENT DOCUMENTS

| | | | |
|---|---|---|---|
| 5,554,033 A | 9/1996 | Bizzi et al. | |
| 5,846,086 A | 12/1998 | Bizzi et al. | |
| 2006/0262120 A1* | 11/2006 | Rosenberg | ............... 345/473 |
| 2009/0298649 A1* | 12/2009 | Dyer et al. | .................. 482/4 |
| 2010/0113117 A1* | 5/2010 | Ku et al. | ..................... 463/7 |
| 2010/0190610 A1* | 7/2010 | Pryor et al. | .................. 482/8 |
| 2010/0323846 A1* | 12/2010 | Komatsu et al. | ............. 482/9 |
| 2011/0217683 A1* | 9/2011 | Vlasenko et al. | ......... 434/257 |
| 2011/0218462 A1* | 9/2011 | Smith | ....................... 600/595 |

(Continued)

FOREIGN PATENT DOCUMENTS

JP    2000-504854 A    4/2000

*Primary Examiner* — Phi Hoang
(74) *Attorney, Agent, or Firm* — Lerner, David, Littenberg, Krumholz & Mentlik, LLP

(57) ABSTRACT

There is provided an image processing device including a recognition unit that recognizes exercise of a person reflected in an input image, and a display control unit that superimposes on the input image a virtual object varying according to effectiveness of the exercise recognized by the recognition unit. The image processing device further includes a score calculation unit that calculates a score denoting the effectiveness of the exercise recognized by the recognition unit, and the display control unit superimposes on the input image the virtual object representing greatness of the score calculated by the score calculation unit.

18 Claims, 21 Drawing Sheets

(56) References Cited

U.S. PATENT DOCUMENTS

2011/0300994 A1* 12/2011 Verkaaik et al. ............... 482/51
2011/0320949 A1* 12/2011 Ohki et al. .................... 715/727
2012/0051588 A1* 3/2012 McEldowney ................ 382/103
2012/0058824 A1* 3/2012 Raptis et al. .................... 463/36
2013/0072353 A1* 3/2013 Alessandri et al. ............... 482/8

* cited by examiner

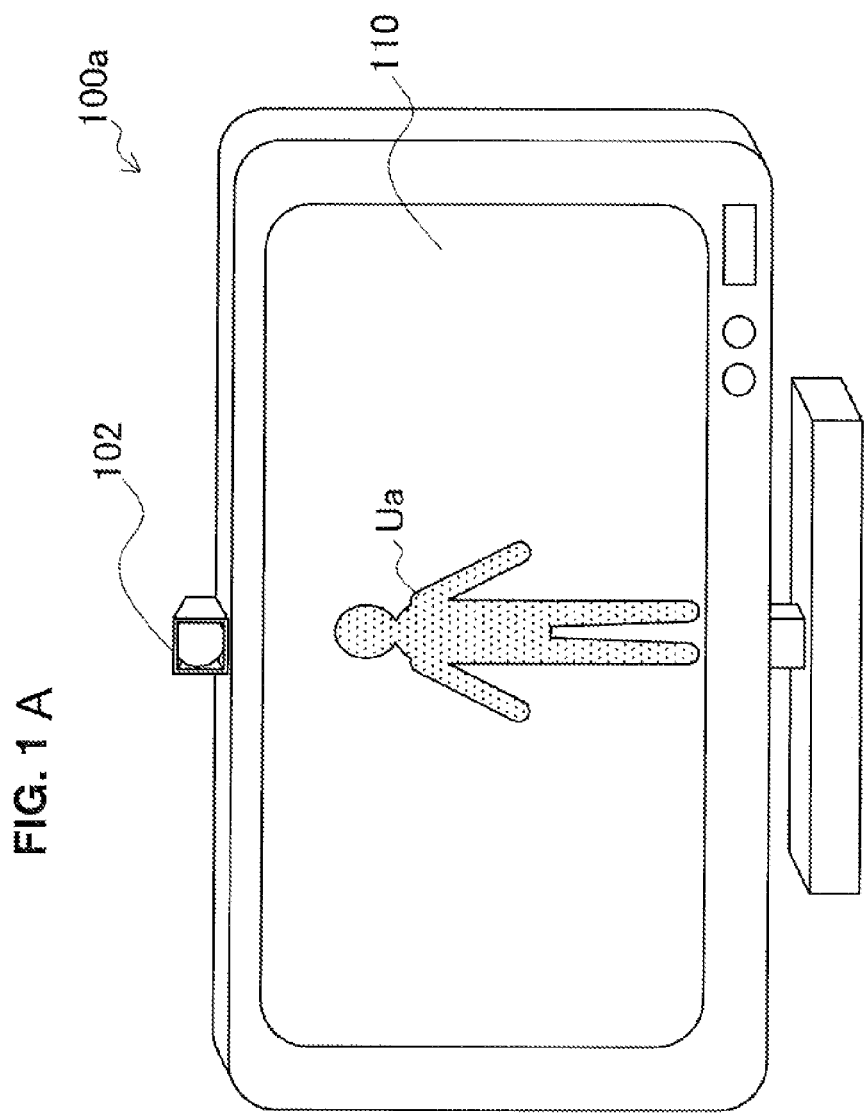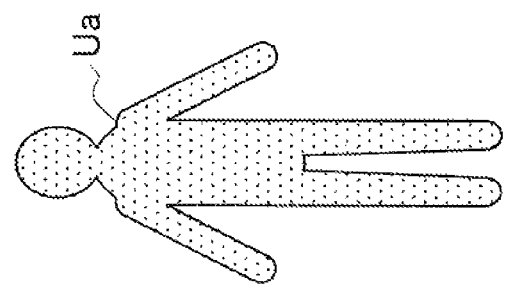

| SECTION | EFFECTIVENESS SCORE | ACCUMULATED VALUE |
|---------|---------------------|-------------------|
| SEG01   | 4                   | 4                 |
| SEG02   | 4                   | 8                 |
| SEG03   | 3                   | 11                |
| :       | :                   | :                 |
| SEG10   | 2                   | 32                |

SCORE CALCULATION RESULTS

OVERLAPPING RATIO→LARGE
⇩
EFFECTIVENESS SCORE→LARGE

FIG. 6D
EXERCISE RECOGNITION RESULT (USER Ua)
| SECTION | NECESSARY TIME | MAXIMUM ACCELERATION |
|---|---|---|
| SEG01 | 2.0 | 1.2 |
| SEG02 | 2.2 | 1.1 |
| SEG03 | 2.4 | 1.1 |
| : | : | : |
| SEG10 | 3.5 | 0.9 |
| EFFECTIVENESS SCORE |
|---|
| 4 |
| 3 |
| 3 |
| : |
| 2 |
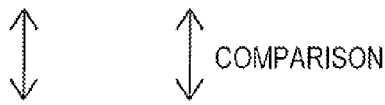
COMPARISON
| SECTION | NECESSARY TIME | MAXIMUM ACCELERATION |
|---|---|---|
| 01 | 2.0 | 1.4 |
| 02 | 2.0 | 1.4 |
| 03 | 2.0 | 1.4 |
| : | : | : |
| 10 | 2.4 | 1.1 |
| : | : | : |
EXERCISE MODEL (Mc)

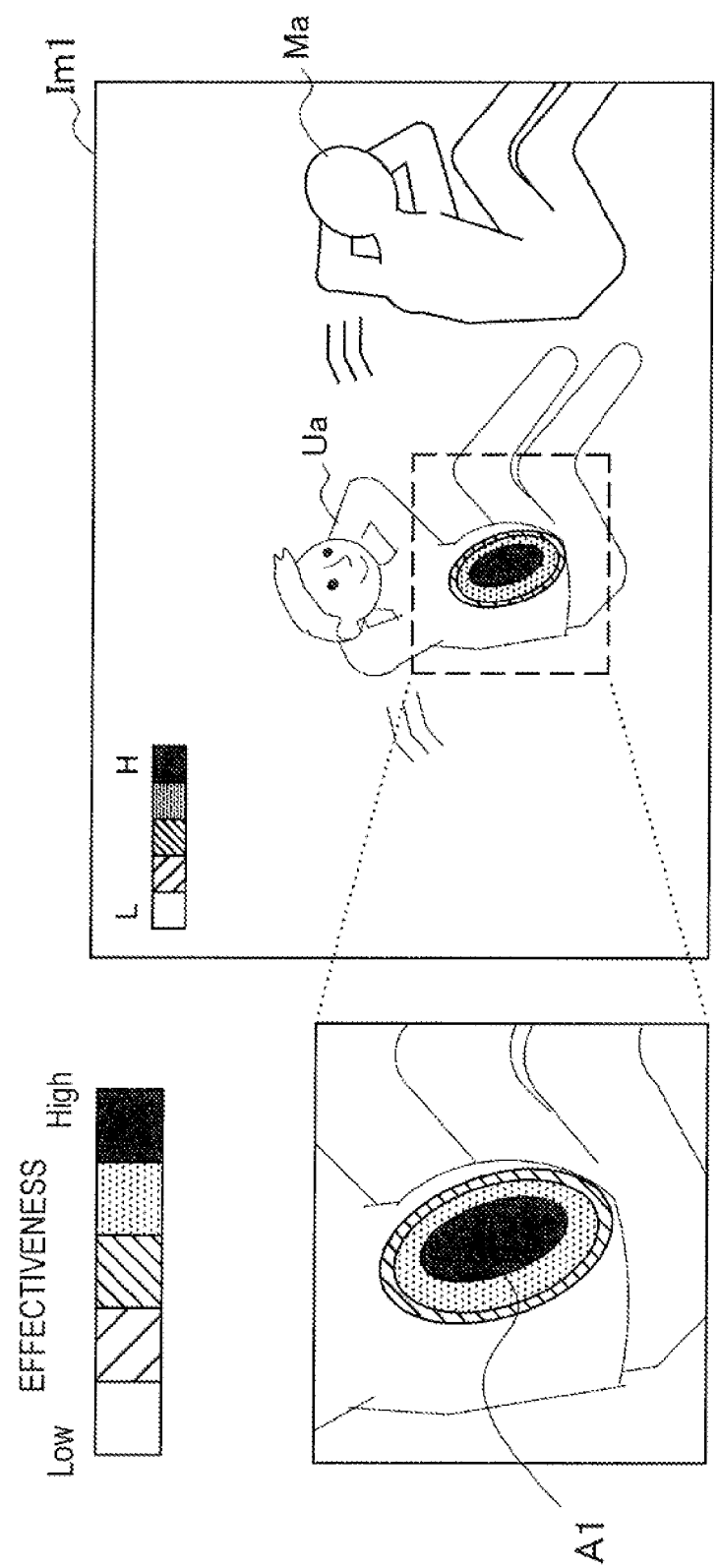

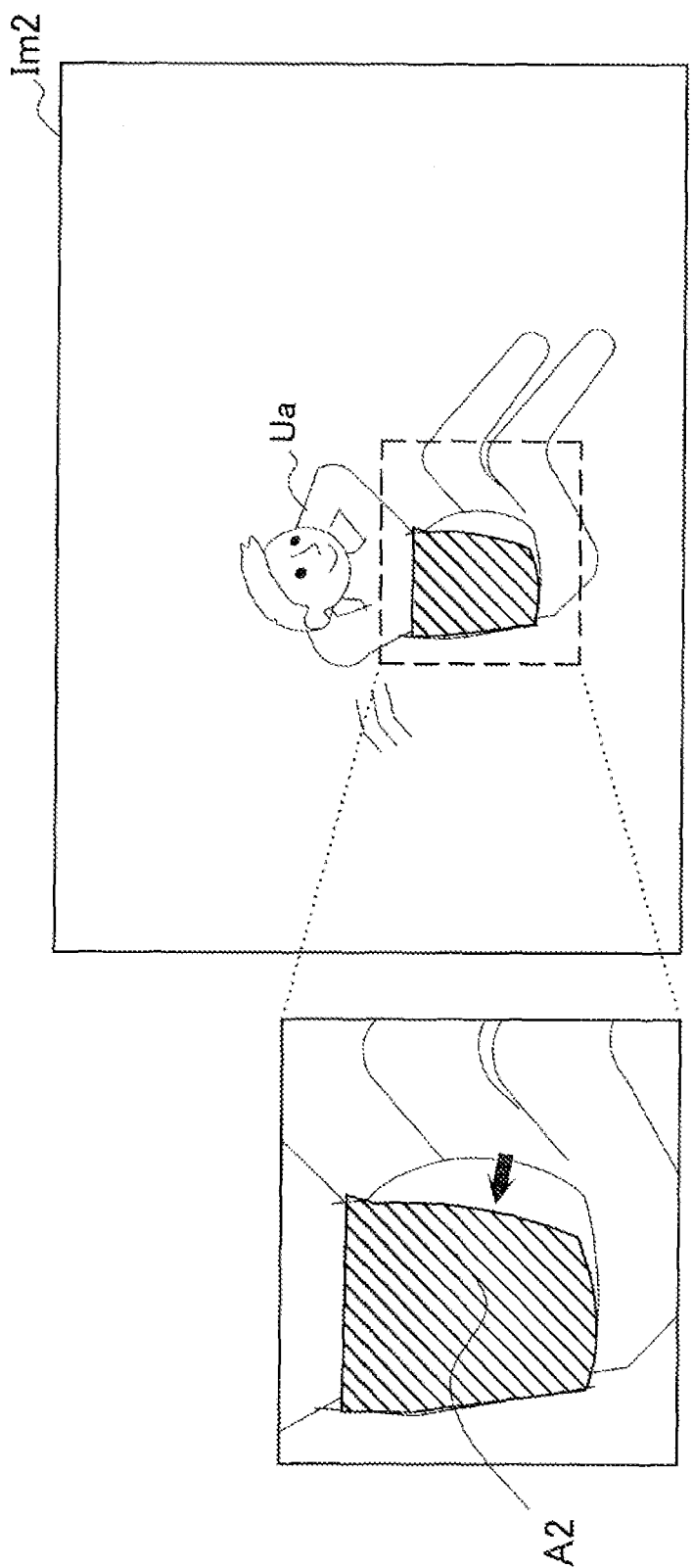

| PERSON ID | DATE | AMOUNT EATEN | AMOUNT OF EXERCISE | AMOUNT OF SLEEP |
|---|---|---|---|---|
| UA | 11/1/2011 | X1 | E1 | L1 |
| UA | 11/2/2011 | X2 | E2 | L2 |
| UA | 11/3/2011 | X3 | E3 | L3 |
| : | : | : | : | : |

LIVING HISTORY DATA

IMAGE PROCESSING DEVICE, IMAGE PROCESSING METHOD, AND PROGRAM

CROSS-REFERENCE TO RELATED APPLICATION

The present application claims priority from Japanese Patent Application No. JP 2011-249751 filed in the Japanese Patent Office on Nov. 15, 2011, the entire content of which is incorporated herein by reference.

BACKGROUND

The present disclosure relates to an image processing device, an image processing method, and a program.

Recently, exercise for maintaining or improving health or recovering from wounds has become a part of daily life. Muscular strength training, rehabilitation, shape-up, and the like are examples of such exercise. Japanese Unexamined Patent Application Publication (Translation of PCT Application) No. 2000-504854 proposes a technique for showing an image sequence of exercise of a teacher and an image sequence of exercise of a student in parallel on a display. According to this technique, it becomes easy for a user as a student to copy exercise of a teacher, and exercise capacity of the user is expected to be more efficiently improved.

SUMMARY

However, in general, it is said that in order to make exercise efficient, it is important to give sufficient feedback about effectiveness of the exercise to a person who performs the exercise. The technique proposed by Japanese Unexamined Patent Application Publication (Translation of PCT Application) No. 2000-504854 only presents exercise to be regarded as an objective and does not give a user sufficient feedback. For example, when a person's distance from an objective exercise or improvement in the person's health is presented in a visualized form, the person's motivation to continue the exercise is boosted, and also the person is motivated to perform effective exercise by improving his/her own exercise.

Accordingly, it is preferable to provide a structure capable of presenting feedback about effectiveness of exercise to a user in a visualized form.

According to an embodiment of the present disclosure, there is provided an image processing device which includes a recognition unit that recognizes exercise of a person reflected in an input image, and a display control unit that superimposes on the input image a virtual object varying according to effectiveness of the exercise recognized by the recognition unit.

According to another embodiment of the present disclosure, there is provided an image processing method which includes recognizing exercise of a person reflected in an input image, and superimposing on the input image a virtual object varying according to effectiveness of the recognized exercise.

According to still another embodiment of the present disclosure, there is provided a program for causing a computer which controls an image processing device to function as a recognition unit for recognizing exercise of a person reflected in an input image, and a display control unit for superimposing on the input image a virtual object varying according to effectiveness of the exercise recognized by the recognition unit.

According to the embodiments of the present disclosure, it is possible to present feedback about effectiveness of exercise to a user in a visualized form.

BRIEF DESCRIPTION OF THE DRAWINGS

FIG. 1A is a first explanatory diagram illustrating an outline of an image processing device related to the present disclosure;

FIG. 6D is an explanatory diagram illustrating a fourth method for calculating an effectiveness score;

FIG. 7A is an explanatory diagram illustrating a first example of a virtual object displayed in the first embodiment;

FIG. 7B is an explanatory diagram illustrating a second example of a virtual object displayed in the first embodiment;

DETAILED DESCRIPTION OF THE EMBODIMENT(S)

Figure 1B:
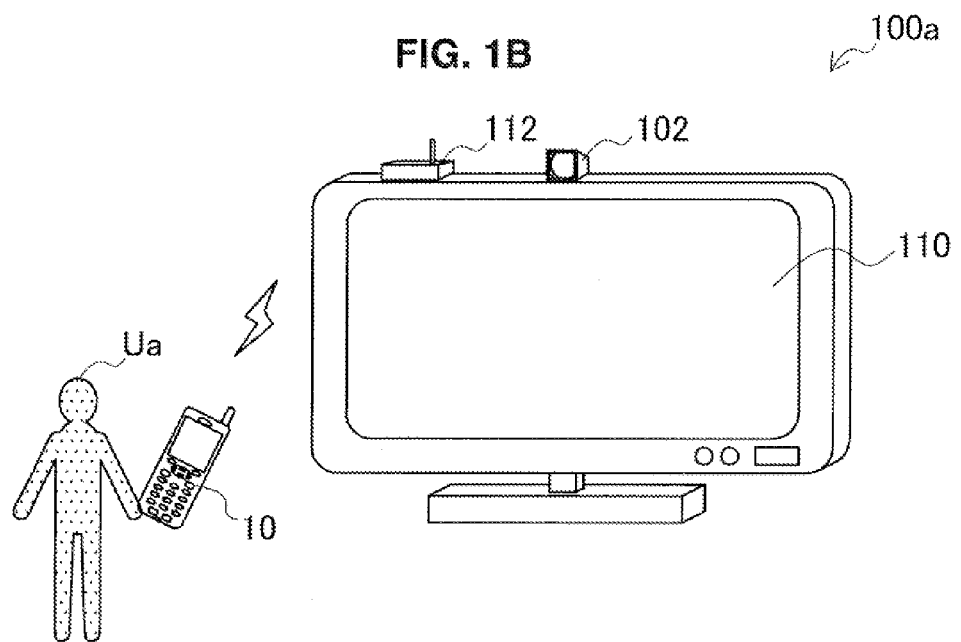
FIG. 1B is a second explanatory diagram illustrating an outline of an image processing device related to the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Descriptions will be given in the following order.
1. Outline
2. First Embodiment
   2-1. Hardware Configuration
   2-2. Functional Configuration
   2-3. Flow of Process
   2-4. Summary of First Embodiment
3. Second Embodiment
   3-1. Functional Configuration
   3-2. Flow of Process
   3-3. Summary of Second Embodiment
4. Third Embodiment
   4-1. Functional Configuration
   4-2. Flow of Process
   4-3. Summary of Third Embodiment

1. Outline

Figure 1C:
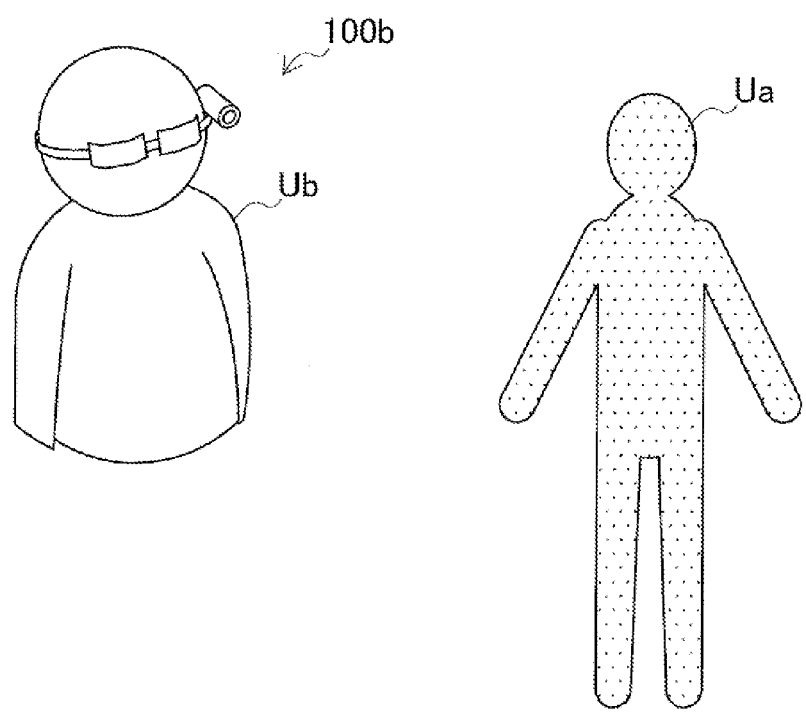
FIG. 1C is a third explanatory diagram illustrating an outline of an image processing device related to the present disclosure.

FIG. 1A to FIG. 1C are explanatory diagrams illustrating an outline of an image processing device related to the present disclosure. Referring to FIG. 1A, an image processing device 100a is shown by way of example. The image processing device 100a includes an imaging unit 102 which has a lens directed toward an exerciser, and a display unit 110 which displays an image. In the example of FIG. 1A, a user Ua is standing in front of the image processing device 100a, and an image of the user Ua taken by the imaging unit 102 is displayed by the display unit 110. The image processing device 100a acquires such a captured image as an input image, and performs a variety of image processes for supporting exercise which will be described in detail later. In such a situation, the user Ua performs exercise, for example, muscular strength training, rehabilitation, shape-up, and the like.

In an example of FIG. 1B, the image processing device 100a further includes a communication unit 112. The communication unit 112 communicates with a terminal device 10 manipulated by, for example, the user Ua. In an image process performed for an input image, the image processing device 100a may utilize additional data acquired through such a communication connection.

In FIG. 1A and FIG. 1B, a digital television device is shown as an example of the image processing device 100a. However, the image processing device 100a is not limited to this example. The image processing device 100a may be an arbitrary device, for example, a desktop PC, a tablet PC, a notebook PC, a smart phone, a digital camera, a gaming terminal, or the like. Also, a screen of the display unit 110 of the image processing device 100a may be a screen, on a surface of which a half mirror is installed. In this case, the user Ua can see his/her own image reflected by the half mirror and also an image partially displayed by the display unit 110 during exercise.

Referring to FIG. 1C, an image processing device 100b is shown as another example. The image processing device 100b is a wearable device having a head mount display. A user Ub is equipped with the image processing device 100b. When the user Ub exercises, the image processing device 100b may photograph a part of the body (for example, an arm and the like) of the user Ub. Alternatively, the image processing device 100b may photograph the exercising user Ua. An image that has been taken and processed by the image processing device 100b is seen by the user Ub through the head mount display. The head mount display of the image processing device 100b may be a see-through type or a non see-through type.

In three embodiments which are described in subsequent sections and related to the present disclosure, feedback about effectiveness of exercise is presented by such a device to a user in a visualized form. In the following descriptions, the image processing devices 100a and 100b are generically referred to as an image processing device 100.

2. First Embodiment

2-1. Hardware Configuration

Figure 2:
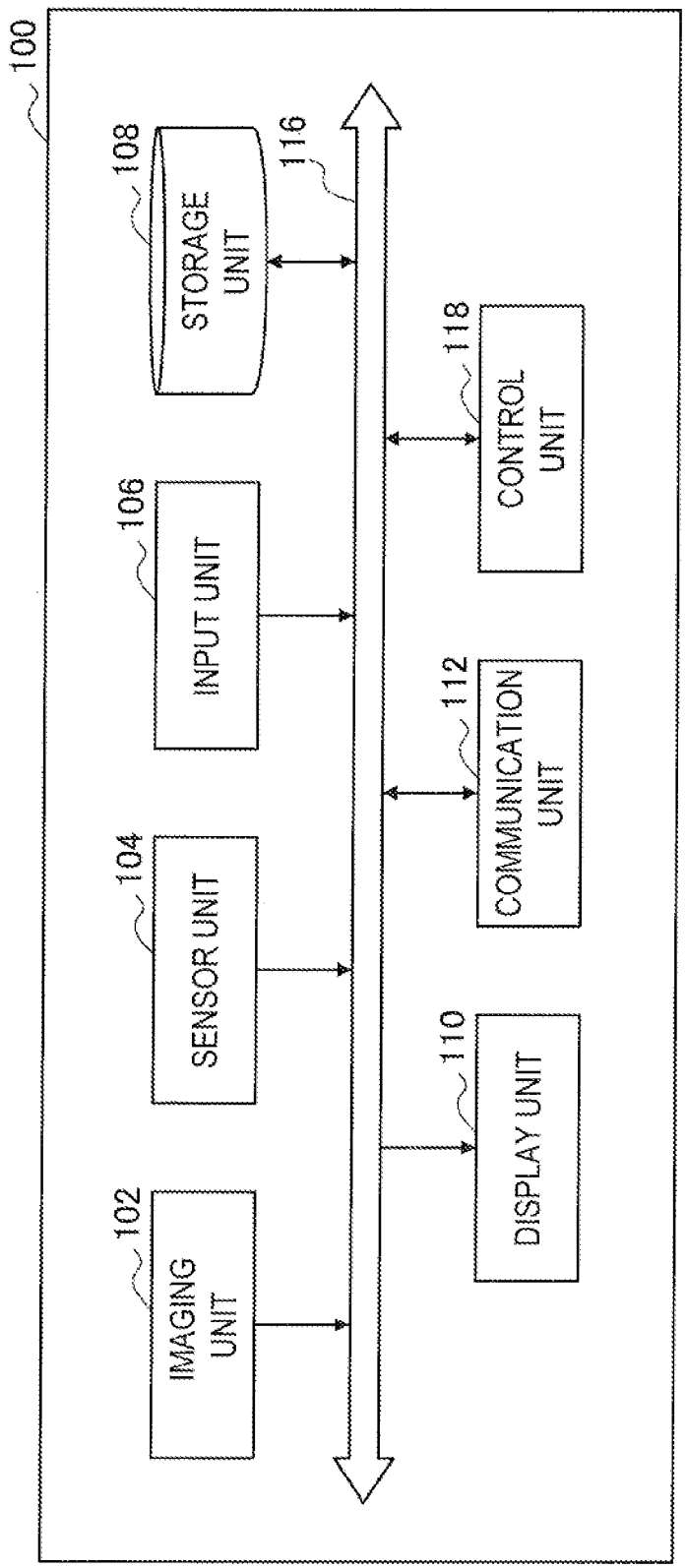
FIG. 2 is a block diagram showing an example of a hardware configuration of an image processing device related to an embodiment.

FIG. 2 is a block diagram showing an example of a hardware configuration of the image processing device 100 related to the first embodiment. Referring to FIG. 2, the image processing device 100 includes an imaging unit 102, a sensor unit 104, an input unit 106, a storage unit 108, a display unit 110, a communication unit 112, a bus 116, and a control unit 118.

(1) Imaging Unit

The imaging unit 102 is a camera module which takes an image. The imaging unit 102 photographs a subject using an imaging element such as a Charge Coupled Device (CCD), a Complementary Metal Oxide Semiconductor (CMOS), or the like, and generates a captured image. It is not necessary that the imaging unit 102 be a part of the image processing device 100. For example, an imaging device which is connected with the image processing device 100 by wire or wirelessly may be handled as the imaging unit 102.

(2) Sensor Unit

The sensor unit 104 is a sensor module which generates sensor data for supporting a process performed in the image processing device 100. For example, the sensor unit 104 may include a myoelectric sensor which senses motion of a user's muscle through an electrode attached to the user's skin. Also, the sensor unit 104 may include an infrared temperature sensor which measures a temperature of a user's body surface. Further, the sensor unit 104 may include an accelerometer which measures acceleration applied to a specific part of the user.

(3) Input Unit

The input unit 106 is an input device which is used for a user to manipulate the image processing device 100 or input information in the image processing device 100. The input unit 106 may include a touch sensor which detects a touch on, for example, the screen of the display unit 110 by a user. Instead of (or in addition to) the touch sensor, the input unit 106 may include a pointing device such as a mouse, a touch pad, and the like. Furthermore, the input unit 106 may include another type of input device such as a keyboard, a keypad, a button, a switch, a remote controller, or the like.

(4) Storage Unit

The storage unit 108 includes a storage medium such as semiconductor memory or a hard disk, and stores a program and data for a process by the image processing device 100. The data stored in the storage unit 108 may include, for example, captured image data generated by the imaging unit 102, sensor data generated by the sensor unit 104, and a variety of data in a database which will be described later. Also, some or all of programs and data described in this specification can be acquired from an external data source (for example, a data server, a network storage, an external memory) without being stored in the storage unit 108.

(5) Display Unit

The display unit 110 is a display module including a Liquid Crystal Display (LCD), Organic Light-Emitting Diode (OLED), Cathode Ray Tube (CRT), or the like. In this embodiment, the display unit 110 can be used to superimpose a virtual object for supporting a user's exercise on an input image. It is also not necessary that the display unit 110 be a part of the image processing device 100. For example, a display device which is connected with the image processing device 100 by wire or wirelessly may be handled as the display unit 110.

(6) Communication Unit

The communication unit 112 is a communication interface which relays communication between the image processing device 100 and another device. The communication unit 112 supports an arbitrary wireless communication protocol or a wired communication protocol, thereby establishing a communication connection with another device.

(7) Bus

The bus 116 connects the imaging unit 102, the sensor unit 104, the input unit 106, the storage unit 108, the display unit 110, the communication unit 112, and the control unit 118 with each other.

(8) Control Unit

The control unit 118 corresponds to a processor such as a Central Processing Unit (CPU), a Digital Signal Processor (DSP), or the like. The control unit 118 executes a program stored in the storage unit 108 or another storage medium, thereby causing various functions of the image processing device 100, which will be described later, to be performed.

2-2. Functional Configuration

Figure 3:
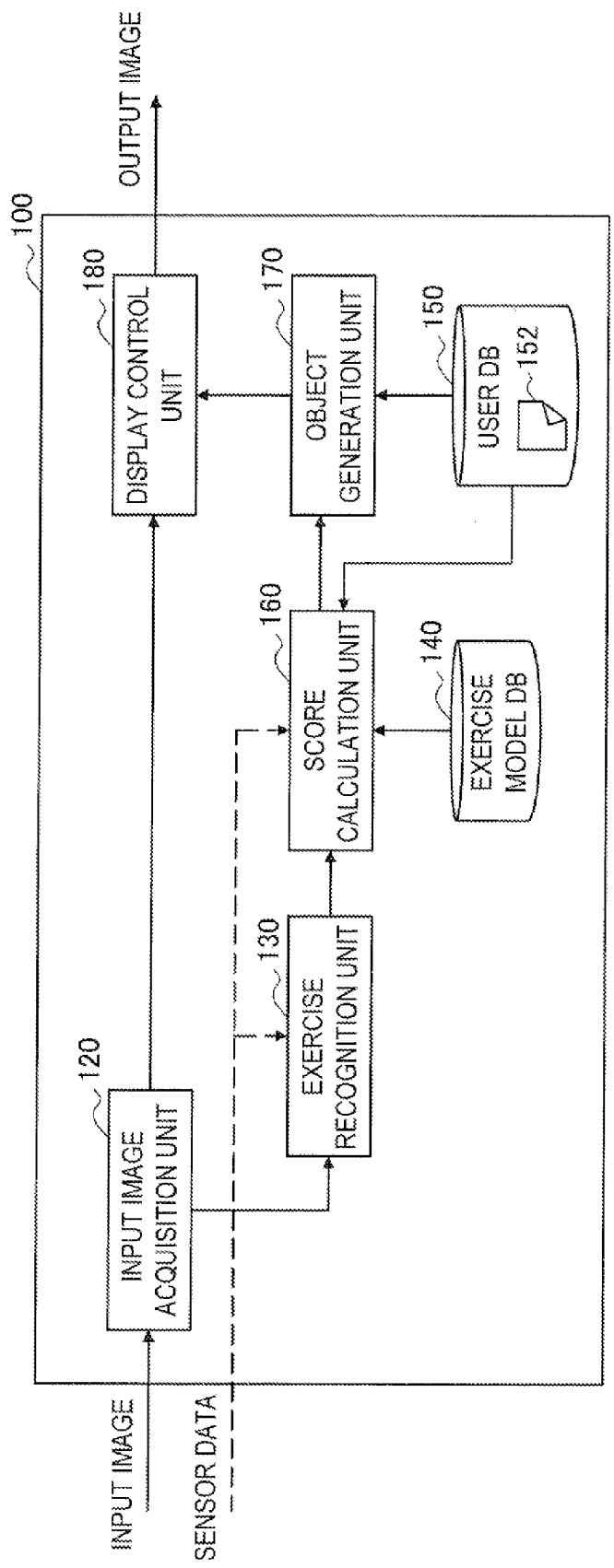
FIG. 3 is a block diagram showing an example of a configuration of logical functions of an image processing device related to a first embodiment.

FIG. 3 is a block diagram showing an example of a configuration of logical functions implemented by the storage unit 108 and the control unit 118 of the image processing device 100 shown in FIG. 2. Referring to FIG. 3, the image processing device 100 includes an input image acquisition unit 120, an exercise recognition unit 130, an exercise model database (DB) 140, a user DB 150, a score calculation unit 160, an object generation unit 170, and a display control unit 180.

(1) Input Image Acquisition Unit

The input image acquisition unit 120 acquires a captured image generated by the imaging unit 102 as an input image. In the input image, an exerciser such as the user Ua or Ub exemplified in FIG. 1A to FIG. 1C or the like is shown. A series of input images acquired by the input image acquisition unit 120 typically constitute a moving picture. The input image acquisition unit 120 sequentially outputs the acquired input image to the exercise recognition unit 130 and the display control unit 180.

(2) Exercise Recognition Unit

The exercise recognition unit 130 recognizes exercise of the person reflected in the input image from the input image acquisition unit 120. The exercise recognized by the exercise recognition unit 130 may be any exercise such as a joint bending and straightening exercise (for example, an abdominal exercise or a squat exercise), running, dance, yoga, aerobics, a sports motion (for example, a golf or tennis swing), or the like. The exercise recognition unit 130 recognizes the exercise of the person reflected in the input image according to known gesture recognition technology. Also, the exercise recognition unit 130 may recognize the exercise of the person reflected in the input image using sensor data from an accelerometer.

Figure 4:
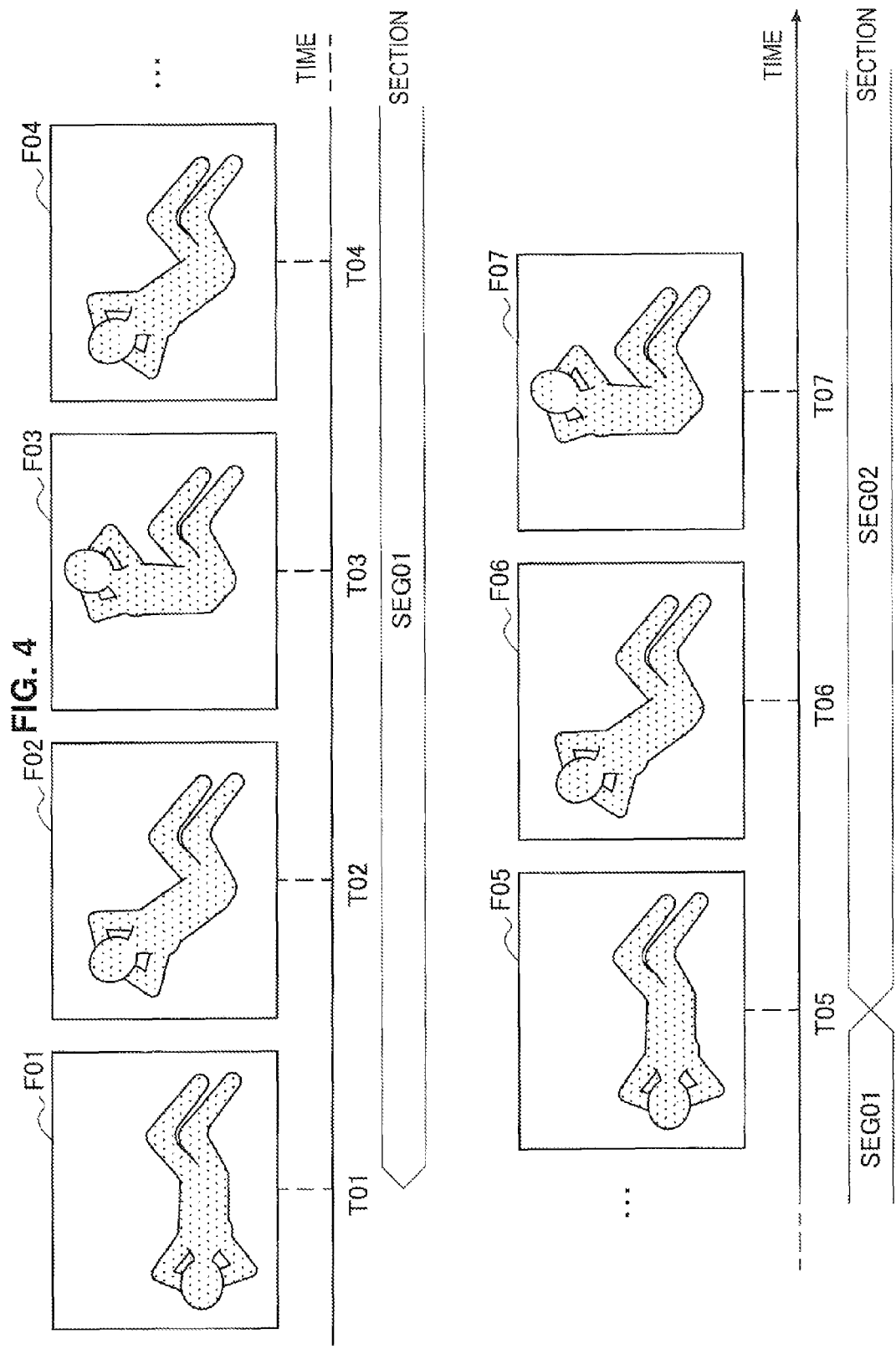
FIG. 4 is an explanatory diagram illustrating an example of an exercise recognition process by an exercise recognition unit exemplified in FIG. 3.

FIG. 4 is an explanatory diagram illustrating an example of an exercise recognition process by the exercise recognition unit 130. Referring to FIG. 4, seven frames F01 to F07 included in a series of input images are shown along a time axis. In frames F01 to F04, one set of an abdominal exercise of a person reflected in these frames is shown. The next set of the abdominal exercise is reflected in the frame F05 and the following frames. The exercise recognition unit 130 recognizes the one set of the abdominal exercise as one unit of gesture, and determines a section corresponding to each recognized unit of gesture on the time axis. In the example of FIG. 4, a section SEG01 corresponding to the frames F01 to F04 and a section SEG02 corresponding to the frames F05 to F07 are determined. For every section determined in this way, the score calculation unit 160 which will be described later calculates a score showing effectiveness of the exercise recognized by the exercise recognition unit 130.

(3) Exercise Model DB 140

The exercise model DB 140 is a DB in which exercise models that are data obtained by modeling exercise regarded as an objective are accumulated. An exercise model may be moving picture data reflecting an exerciser, frame data including a set of the exerciser's feature point positions, numeric data including the number of times of the exercise regarded as an objective and parameters such as strength and the like, or a combination of these pieces of data. In this embodiment, an exercise model is data obtained by modeling exercise of a person who is a teacher in advance. From a plurality of exercise models obtained by modeling exercises of teachers whose attributes such as age, sex, and the like are different from each other, an exercise model appropriate for a user may be able to be selected. In another embodiment, an exercise model is adaptively generated according to a history and an objective of each individual user's exercise.

(4) User DB 150

The user DB 150 is a DB in which a variety of data that is prepared for each individual user is accumulated. In this embodiment, the user DB 150 stores attribute date 152 which may include basic attributes of a user such as age, sex, and the like, and body type attributes such as height, sitting height, chest size, waist size, and the like.

(5) Score Calculation Unit

The score calculation unit 160 calculates a score showing effectiveness of the exercise recognized by the exercise recognition unit 130. More specifically, in this embodiment, the score calculation unit 160 first acquires any of exercise models that are stored by the exercise model DB 140. The score calculation model 160 may selectively acquire an exercise model appropriate for the basic attributes of the exerciser from a plurality of exercise models. Also, the score calculation model 160 may modify an acquired exercise model according to the body type attributes of the exerciser (for example, perform normalization so that the height of a teacher becomes the same as the height of the exerciser). When the exercise is recognized by the exercise recognition unit 130, the score calculation unit 160 calculates an effectiveness score for every section determined by the exercise recognition unit 130 on the basis of a difference between the recognized exercise and an exercise model.

Figures 5, 6A:
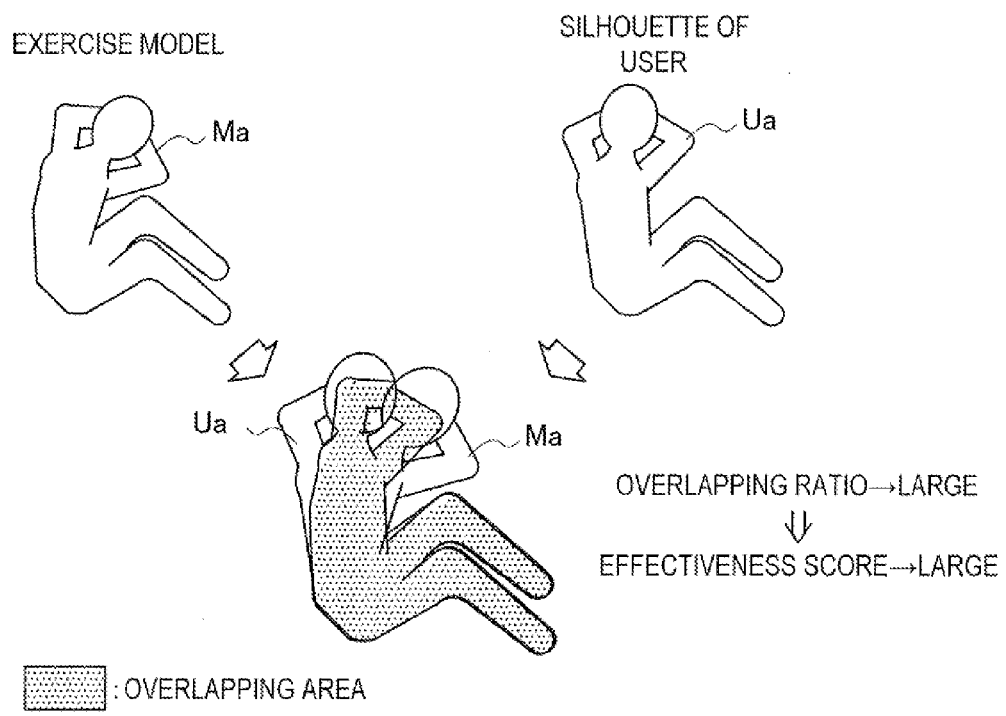
FIG. 5 is an explanatory diagram illustrating an example of an effectiveness score calculated by a score calculation unit exemplified in FIG. 3.
FIG. 6A is an explanatory diagram illustrating a first method for calculating an effectiveness score.

FIG. 5 is an explanatory diagram illustrating an example of an effectiveness score calculated by the score calculation unit 160. Referring to FIG. 5, calculation results of effectiveness scores are shown in a table. In the example of FIG. 5, all effectiveness scores calculated for the sections SEG01 and SEG02 are four. An effectiveness score calculated for a section SEG03 is three. An effectiveness score calculated for a section SEG10 is two. In the example of FIG. 5, effectiveness scores show values from one to five in five levels, and the greater the value, the more effective the exercise is. However, effectiveness scores are not limited to this example, and effectiveness scores defined in other forms may be used. Four example methods for calculating an effectiveness score will be described below with reference to FIG. 6A to FIG. 6D.

(5-1) First Method

FIG. 6A is an explanatory diagram illustrating a first method for calculating an effectiveness score. On the upper left side of the drawing, a silhouette (for example, difference from a background) of a teacher is shown that is reflected in the exercise model Ma, which is moving picture data. On the upper right side of the drawing, a silhouette of the user Ua extracted from an input image is shown. The score calculation unit 160 overlaps these two silhouettes, and increases an effective score value as a ratio of an overlapping area occupied by these silhouettes increases.

(5-2) Second Method

Figure 6B:
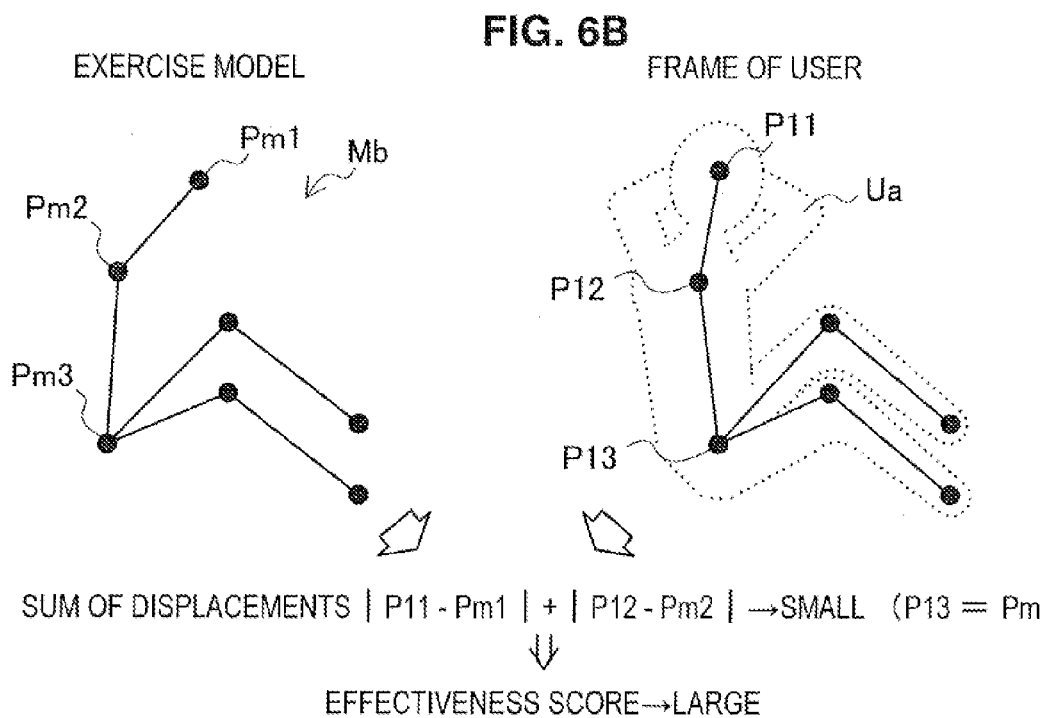
FIG. 6B is an explanatory diagram illustrating a second method for calculating an effectiveness score.

FIG. 6B is an explanatory diagram illustrating a second method for calculating an effectiveness score. On the upper left side of the drawing, three feature point positions Pm1, Pm2 and Pm3 constituting the teacher's frame included in an exercise model Mb which is frame data are shown. On the upper right side of the drawing, three feature point positions P11, P12 and P13 constituting the user's frame extracted from the input image are shown. The feature point positions Pm1 and P11 may correspond to heads, the feature point positions Pm2 and P12 may correspond to shoulders, and the feature point positions Pm3 and P13 may correspond to hip joints. The score calculation unit 160 adjusts, for example, the feature point positions Pm3 and P13 to overlap, and then calculates the sum of a displacement from the position Pm1 to the position P11 and a displacement from the position Pm2 to the position P12, increasing an effectiveness score value as the calculated sum decreases.

(5-3) Third Method

Figure 6C:
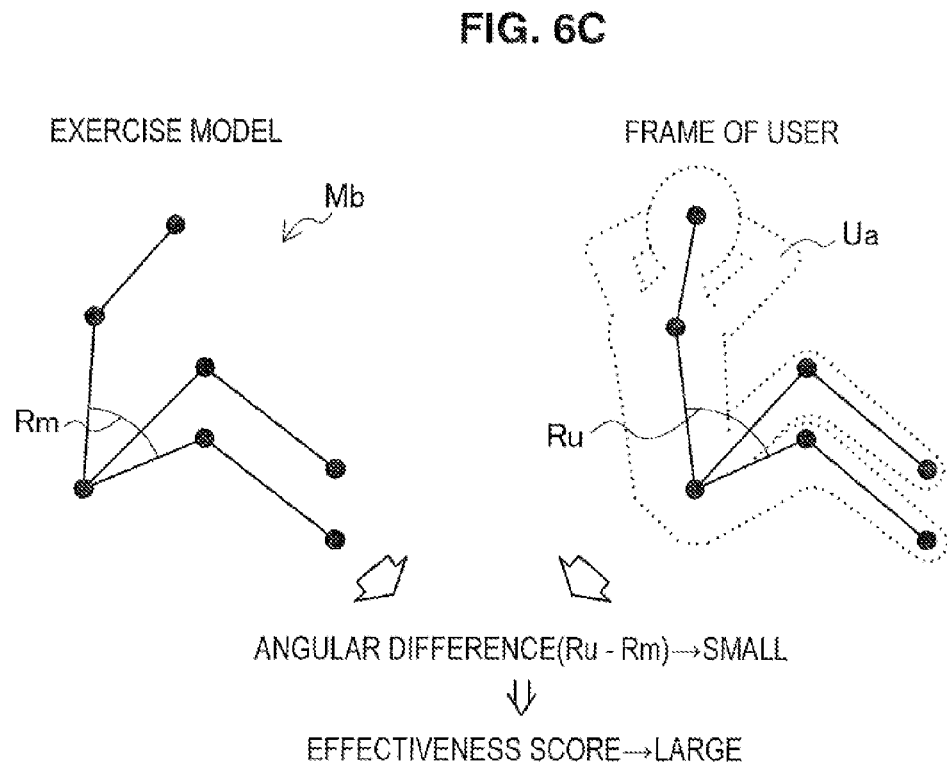
FIG. 6C is an explanatory diagram illustrating a third method for calculating an effectiveness score.

FIG. 6C is an explanatory diagram illustrating a third method for calculating an effectiveness score. FIG. 6C shows again the exercise model Mb as frame data exemplified in FIG. 6B and the frame of the user Ua extracted from the input image. The score calculation unit 160 calculates an angle Rm of the teacher's hip joint and an angle Ru of the hip joint of the user Ua from these pieces of frame data, thereby calculating an angular difference Ru−Rm. Then, the score calculation unit 160 increases an effectiveness score value as the calculated angular difference decreases.

The above-described first to third methods may be applied to all frames corresponding to each section or one or a plurality of frames. For example, the score calculation unit 160 may select one or a plurality of distinguishing frames (for example, a frame reflecting a predetermined pose during exercise) from frames corresponding to each section, and determine a score (the sum of scores) calculated from the selected frames as an effectiveness score of the section.

(5-4) Fourth Method

FIG. 6D is an explanatory diagram illustrating a fourth method for calculating an effectiveness score. In the upper part of FIG. 6D, section-specific necessary times of one unit of exercise and section-specific maximum accelerations, which are statistical values based on sensor data, are shown with respect to the user Ua as exercise recognition results by the exercise recognition unit 130. A maximum acceleration is a parameter that supplementarily denotes effectiveness of the exercise. The lower part of FIG. 6D shows an exercise model Mc that is the same data of a teacher's exercise. The score calculation unit 160 compares such exercise recognition results with an exercise model for every section, and increases an effectiveness score value as values of the recognized exercise become close to values of the exercise model. In the example of FIG. 6D, an effectiveness score of the section SEG01 is calculated to be four, effectiveness scores of the sections SEG02 and SEG03 are calculated to be three, and an effectiveness score of the section SEG10 is calculated to be two.

The score calculation unit 160 may only use any one of the above-described four methods, or combine a plurality of methods through calculation such as weighted addition and the like. In this way, the score calculation unit 160 calculates an effectiveness score that shows effectiveness of the exercise for every section, and outputs the calculated effectiveness scores to the object generation unit 170.

(6) Object Generation Unit

The object generation unit 170 generates a virtual object varying according to effectiveness of the recognized exercise. A virtual object generated by the object generation unit 170 may typically be an object that represents the greatness of an effectiveness score calculated by the score calculation unit 160. The greatness of an effectiveness score which is regarded as a base for generating a virtual object may be the greatness of an effectiveness score calculated for each section, an accumulated value of the effectiveness scores as exemplified in FIG. 5, or a combination of them. In this embodiment, a virtual object generated by the object generation unit 170 is an object that emphasizes a target region of exercise. A target region of exercise can correspond to, for example, the abdomen in the case of an abdominal exercise, and the femoral region in the case of a squat exercise. A target region of exercise may be defined in advance in connection with a type of the exercise, or dynamically determined such as a region having a high temperature indicated by sensor data from the infrared temperature sensor. A virtual object may emphasize a target region of exercise in a variety of methods. For example, the greatness of an effectiveness score may be represented by the color, the number or the size of a virtual object that imitates a flame or light disposed around a target region. Also, a change in the appearance of a target region may be expressed exaggeratively according to the greatness of an effectiveness score. Some examples of virtual objects that can be generated by the object generation unit 170 will be described in further detail later.

(7) Display Control Unit

The display control unit 180 superimposes a virtual object generated by the object generation unit 170 on the input image from the input image acquisition unit 120, thereby presenting the virtual object to the user. The display control unit 180 may superimpose a virtual object that emphasizes a target region on a position in the input image at which the target region is shown. At this time, the display control unit 180 may enable the user to see and check the image of both the exerciser and the virtual object by setting the virtual object to be translucent. Alternatively, the display control unit 180 may superimpose the virtual object around the exerciser in the input image. Also, the display control unit 180 may superimpose a virtual object that represents a selected exercise model on the input image. Three examples of a virtual object displayed by the display control unit 180 will be described below with reference to FIG. 7A to FIG. 7C.

(7-1) First Example

FIG. 7A is an explanatory diagram illustrating a first example of a virtual object displayed in this embodiment. In FIG. 7A, an output image Im1 is shown as an example that can be displayed by the display unit 110, and the output image Im1 shows the user Ua who is performing an abdominal exercise. Also, in the output image Im1, a virtual object A1 is superimposed on the abdomen of the user Ua that is the target region of the abdominal exercise. The virtual object A1 is an object that emphasizes the target region of the exercise and also represents the greatness of an effectiveness score calculated by the score calculation unit 160 using its color. In the example of FIG. 7A, a color of a central portion of the virtual object A1 is set to represent a high effectiveness score. By looking at the virtual object A1, the user Ua can intuitively and clearly know how much of an effect his/her exercise has on which target region. In addition, a virtual object that represents the exercise model Ma is also superimposed on the output image Im1.

(7-2) Second Example

FIG. 7B is an explanatory diagram illustrating a second example of a virtual object displayed in this embodiment. In FIG. 7B, an output image Im2 is shown as an example that can be displayed by the display unit 110, and the output image Im2 shows the user Ua who is performing an abdominal exercise. Also, in the output image Im2, a virtual object A2 is superimposed on the abdomen of the user Ua that is the target region of the abdominal exercise. The virtual object A2 is an object that emphasizes the target region of the exercise and also exaggeratively represents a change in the appearance of the target region according to the greatness of an effectiveness score. In the example of FIG. 7B, a reduction in the waist size of the user Ua is exaggerated according to the greatness of an effectiveness score. By looking at the virtual object A2, the user Ua can intuitively and clearly know how much of an effect his/her exercise has on which target region. Also, by looking at his/her image that becomes close to an objective, the motivation of the user Ua to exercise can be enhanced.

(7-3) Third Example

Figure 7C:
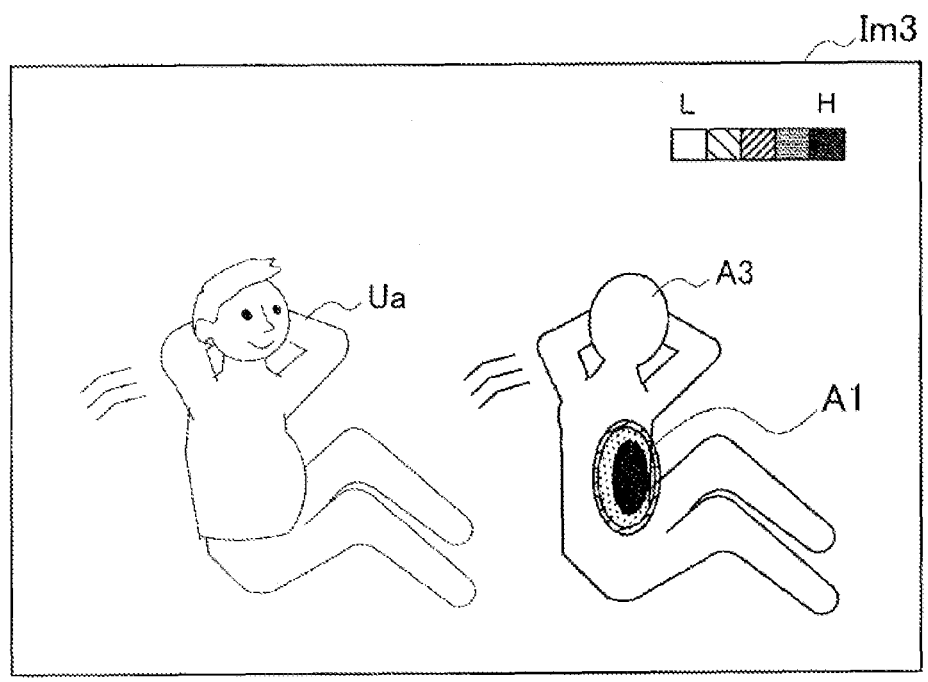
FIG. 7C is an explanatory diagram illustrating a third example of a virtual object displayed in the first embodiment.

FIG. 7C is an explanatory diagram illustrating a third example of a virtual object displayed in this embodiment. In FIG. 7C, an output image Im3 is shown as an example that can be displayed by the display unit 110, and the output image Im3 shows the user Ua who is performing an abdominal exercise. Also, a virtual object A3 representing the user Ua is superimposed on the output image Im3 next to the user Ua. The virtual object A1 that is exemplified in FIG. 7A is further superimposed on the abdomen of the virtual object A3. In the example of FIG. 7C, the image of the user Ua is not hidden by a virtual object, and thus the user Ua can clearly see and check his/her exercise and also know effects of the exercise in parallel.

2-3. Flow of Process

Figure 8:
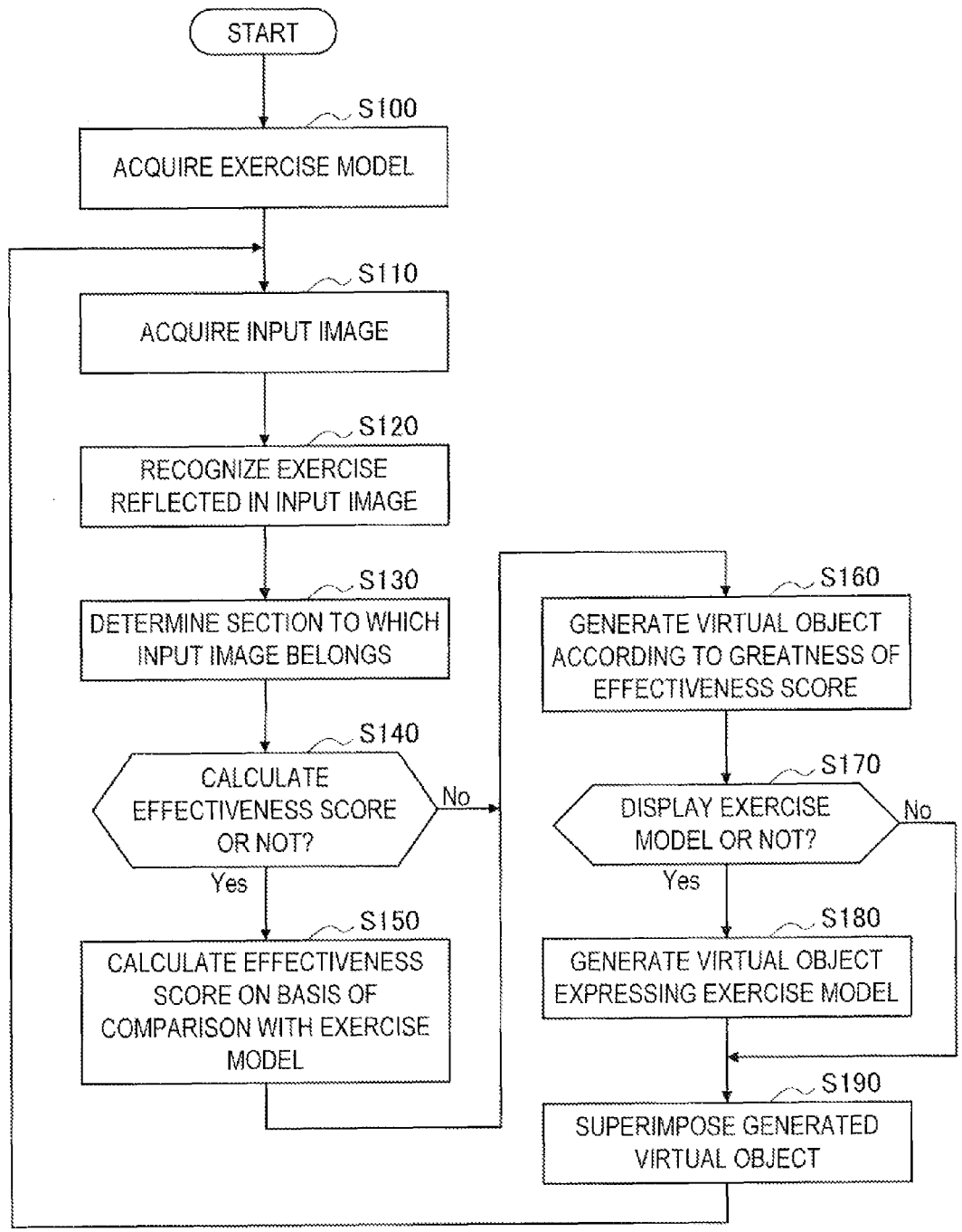
FIG. 8 is a flowchart showing an example of image processing flow related to the first embodiment.

FIG. 8 is a flowchart showing an example of flow of image processing by the image processing device 100 related to this embodiment.

Referring to FIG. 8, around the start of exercise, the score calculation unit 160 acquires any of exercise models stored in the exercise model DB 140 (step S100). A process of the following steps S110 to S190 is repeated for each of a series of input images.

First, the input image acquisition unit 120 acquires a captured image generated by the imaging unit 102 as an input image (step S110).

Next, the exercise recognition unit 130 recognizes the exercise of a person reflected in the input image from the input image acquisition unit 120 (step S120). The exercise recognition unit 130 determines a section on the time axis to which the input image belongs (step S130). For example, when it is recognized that a new unit of gesture is started, the exercise recognition unit 130 can determine that the input image belongs to a new section. Meanwhile, when it is recognized that a gesture continues from a previous input image, the exercise recognition unit 130 can determine that the input image belongs to the same section as the previous input image.

Next, the score calculation unit 160 determines whether or not to calculate an effectiveness score for the input image (step S140). For example, when an effectiveness score is only calculated for a frame reflecting a predetermined pose, and the predetermined pose is not reflected in the input image, calculation of an effectiveness score for the input image can be skipped. When it is determined to calculate the effectiveness score in step S140, the score calculation unit 160 compares the exercise recognized by the exercise recognition unit 130 with the exercise model, and calculates the effectiveness score on the basis of a difference between them (step S150).

Next, the object generation unit 170 generates a virtual object that represents the greatness of the effectiveness score calculated by the score calculation unit 160 (step S160). Here, the generated virtual object may be an object such as the virtual objects A1 to A3 exemplified in FIG. 7A to FIG. 7C. Also, the object generation unit 170 determines whether or not it is necessary to display the exercise model according to a setting (step S170), and also generates a virtual object that represents the exercise model when it is necessary to display the exercise model (step S180).

The display control unit 180 superimposes the virtual objects generated by the object generation unit 170 on the input image, and causes the display unit 110 to display the virtual objects (step S190).

2-4. Summary of First Embodiment

Thus far, the first embodiment of the technology related to the present disclosure has been described. In this embodiment, a virtual object varying according to effectiveness of exercise of a person reflected in an input image is generated, and the generated virtual object is superimposed on the input image. Accordingly, it is possible to present feedback about effectiveness of the exercise to a user in a visualized form.

Also, in this embodiment, effectiveness of exercise is quantitatively calculated as an effectiveness score. An effectiveness score can be calculated on the basis of a difference between exercise and an exercise model regarded as an objective by an exerciser. Accordingly, the greatness of an effectiveness score varies according to the degree of achievement of an objective, and a user's motivation to achieve the objective can be enhanced.

Also, in this embodiment, a virtual object that is superimposed on an input image is an object that emphasizes a target region of exercise. Since a target region of exercise is emphasized by a method in accordance with the greatness of an effectiveness score, a user can intuitively and clearly know how much of an effect the exercise has on which target region.

In addition, an exerciser and a user who looks at an output image from the image processing device 100 may not necessarily be the same person. For example, by making a practical application of the structure provided by the image processing device 100, images are exchanged between a plurality of users as in video chatting to mutually check effects of exercise, and competitive spirit between the users is stimulated, so that the effects of the exercise can be further improved.

3. Second Embodiment

In a second embodiment described in this chapter, an exercise model appropriate for a situation of an exerciser is generated. An image processing device 200 related to this embodiment handles, for example, exercises for rehabilitation. However, this embodiment is not limited to this example, and can also be applied to other types of exercises.

3-1. Functional Configuration

Figure 9:
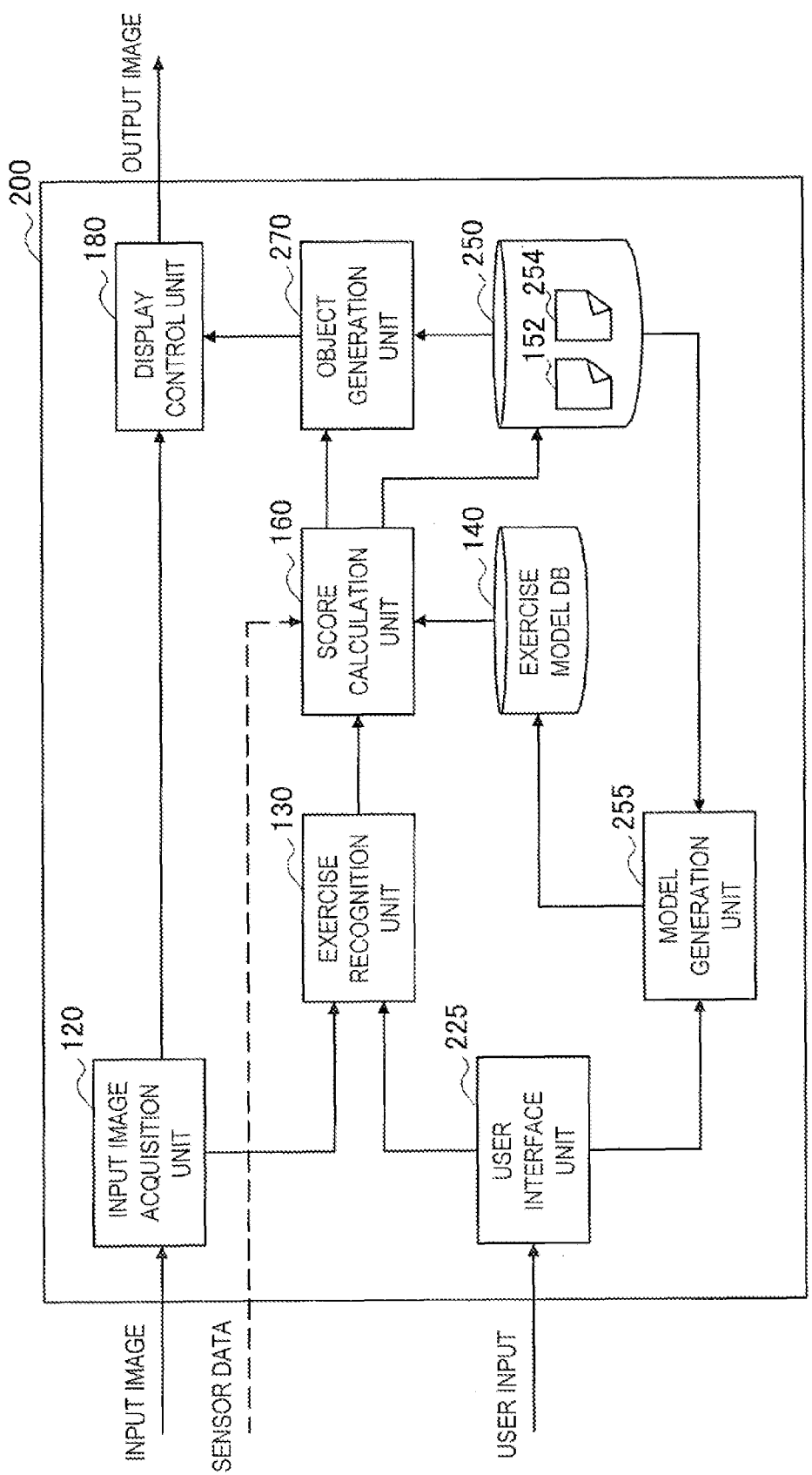
FIG. 9 is a block diagram showing an example of a configuration of logical functions of an image processing device related to a second embodiment.

A hardware configuration of the image processing device 200 may be equivalent to the hardware configuration of the image processing device 100 exemplified in FIG. 2. FIG. 9 is a block diagram showing an example of a configuration of logical functions implemented in the image processing device 200. Referring to FIG. 9, the image processing device 200 includes an input image acquisition unit 120, a user interface unit 225, an exercise recognition unit 130, an exercise model DB 140, a user DB 250, a model generation unit 255, a score calculation unit 160, an object generation unit 270, and a display control unit 180.

(1) User Interface Unit

The user interface unit 225 provides a user with a user interface that receives an input of objective data used for generating an exercise model which will be described later. The objective data can include, for example, a parameter value regarded as an objective of exercise, and a date on which it is necessary to achieve the objective. Types of parameters regarded as objectives of exercise may be any types, for example, bending angles for joint bending and straightening exercises, walking speed for a walking exercise, and the like. Objective data for a rehabilitation exercise may be input by an exercising patient, or a doctor or a trainer who manages the exercise.

(2) User DB

The user DB 250 is a DB in which a variety of data prepared for each individual user is accumulated. The user DB 250 stores the attribute data 152 which has been described in connection with the first embodiment. Further, in this embodiment, the user DB 250 stores exercise history data 254 in which an objective and a record of exercise of each exerciser are maintained. The objective of exercise is given by the objective data acquired through the user interface unit 225. The record of exercise is input and accumulated as a result of exercise recognition from the exercise recognition unit 130 and the score calculation unit 160. The exercise history data 254 is used for generation of an exercise model by the model generation unit 255.

(3) Model Generation Unit

The model generation unit 255 generates an exercise model used for calculating an effectiveness score on the basis of an exercise situation of an exerciser. In this embodiment, an exercise situation is represented by the exercise history data 254 stored by the user DB 250.

Figure 10:
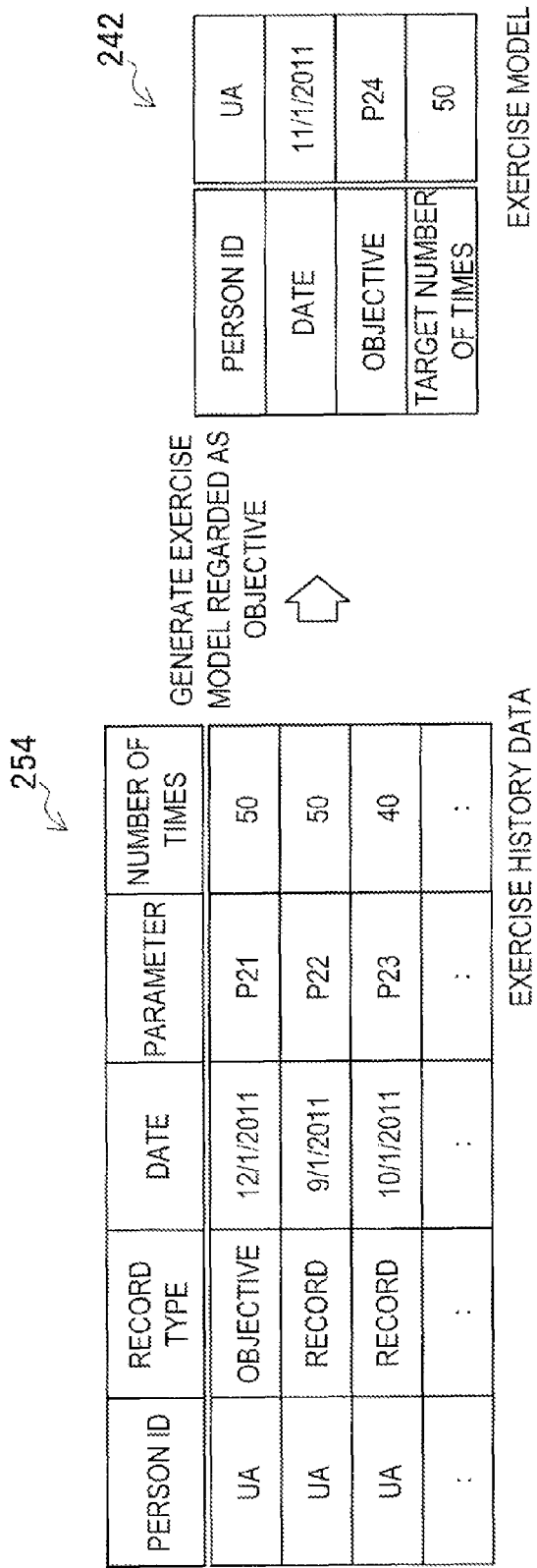
FIG. 10 is an explanatory diagram illustrating an example of a model generation process by a model generation unit exemplified in FIG. 9.

FIG. 10 is an explanatory diagram illustrating an example of a model generation process by the model generation unit 255.

On the left side in FIG. 10, the exercise history data 254 is shown as an example. The exercise history data 254 has five data categories referred to as "Person ID," "Record Type," "Date," "Parameter," and "Number of Times." A "Person ID" is an identifier for uniquely identifying an exerciser. A "Record Type" is a classification value that denotes any of values referred to as "Objective" or "Record." A "Date" denotes a date on which an objective denoted by the corresponding record or a date on which a record denoted by the corresponding record has been made. A "Parameter" denotes a parameter value input as an objective, or an achieved parameter value. A "Number of Times" denotes the number of times of exercise input as an objective, or the number of times that the exercise is achieved.

Using the exercise history data 254 like this, the model generation unit 255 generates an exercise model 242 as exemplified on the right side in FIG. 10 on the basis of an objective and a record of exercise of the exerciser. In the example of FIG. 10, the exercise model 242 denotes that it is necessary for a person whose person ID is "UA" to perform the exercise "50" times "Nov. $1^{st}$, 2011" with an objective of a parameter value "P24." A target parameter value may be calculated by interpolation between a past record value and a future target value. Also, the target parameter value may be calculated by calculating and using general statistical data of a similar person (for example, another rehabilitation patient who has an illness with similar symptoms).

Like in the first embodiment, the exercise recognition unit 130 of the image processing device 200 recognizes exercise of the person reflected in the input image from the input image acquisition unit 120. Then, the score calculation unit 160 calculates an effectiveness score for every section determined by the exercise recognition unit 130 on the basis of a difference between the exercise model generated by the model generation unit 255 and the recognized exercise.

(4) Object Generation unit

The object generation unit 270 generates a virtual object that represents the greatness of the effectiveness score calculated by the score calculation unit 160. In this embodiment, the virtual object generated by the object generation unit 270 may be, for example, an object that exaggeratively represents motion of a target region according to the greatness of the score.

Figure 11:
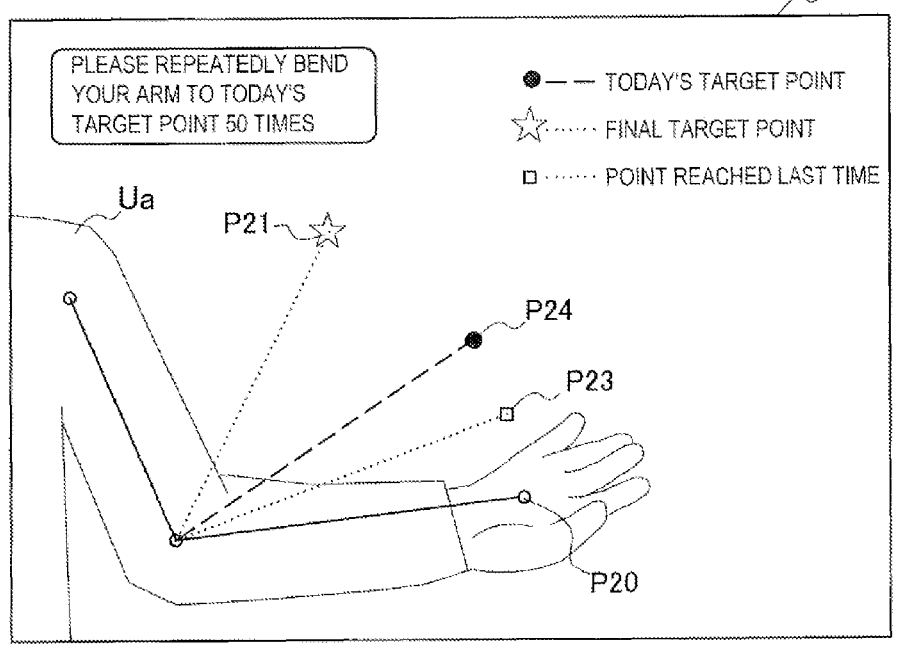
FIG. 11 is an explanatory diagram showing an example of an image displayed upon the start of exercise in the second embodiment.

FIG. 11 is an explanatory diagram showing an example of an image displayed upon the start of exercise in this embodiment. Referring to FIG. 11, a right arm of a user Ua who performs a rehabilitation exercise for an elbow joint is reflected in an output image Im4. A feature point position P21 is a target position that a palm of the right arm will finally reach. A feature point position P23 is a position that the palm of the right arm has reached in a previous rehabilitation exercise. A feature point position P24 is a target position that the palm of the right arm will reach in a rehabilitation exercise of this time. In addition, the output image Im4 may not only be displayed upon the start of the exercise but also may be displayed during the exercise (for example, when the exercise is paused).

Figure 12:
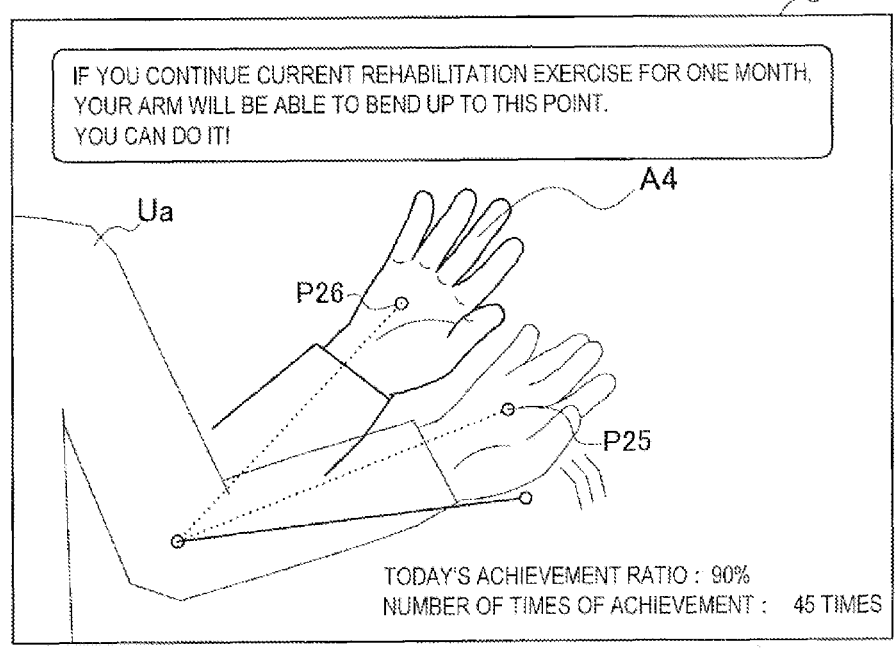
FIG. 12 is an explanatory diagram illustrating an example of a virtual object displayed in the second embodiment.

FIG. 12 is an explanatory diagram illustrating an example of a virtual object displayed in this embodiment. In FIG. 12, an output image Im5 is shown as an example that can be displayed by the display unit 110 of the image processing device 200, and the output image Im5 shows the right arm of the user Ua who is performing a rehabilitation exercise of an elbow. A virtual object A4 is superimposed on the output image Im5. The virtual object A4 is generated by processing an image of the right arm which is the target region of the exercise, and exaggeratively represents motion of the target region according to the greatness of a score. In other words, in the example of FIG. 12, an actual reaching position P25 of the palm differs from a reaching position P26 of a palm of the virtual object A4. The reaching position P26 is determined to be close to the target position P21 as the effectiveness score increases. The virtual object A4 like this is shown to a rehabilitation patient, and the patient thereby becomes aware of his/her image after recovery from symptoms, so that a motivation for the rehabilitation exercise can be enhanced.

3-2. Flow of Process

Figure 13:
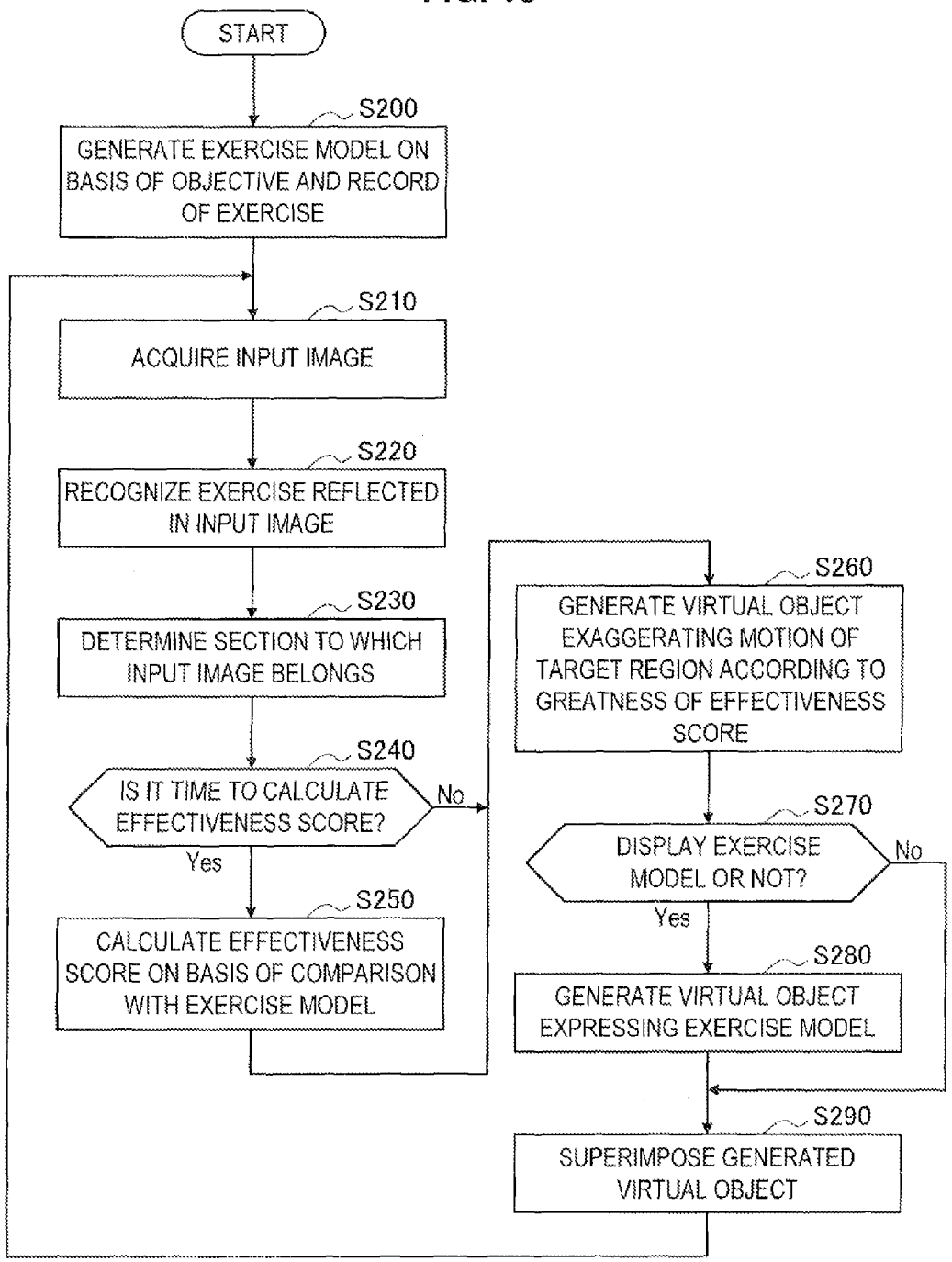
FIG. 13 is a flowchart showing an example of image processing flow related to the second embodiment.

FIG. 13 is a flowchart showing an example of flow of image processing by the image processing device 200 related to this embodiment.

Referring to FIG. 13, around the start of exercise, the model generation unit 255 generates an exercise model on the basis of an objective and a record of the exercise of an exerciser (step S200). A process of the following steps S210 to S290 is repeated for each of a series of input images.

First, the input image acquisition unit 120 acquires a captured image generated by the imaging unit 102 as an input image (step S210).

Next, the exercise recognition unit 130 recognizes the exercise of the person reflected in the input image from the input image acquisition unit 120 (step S220). Then, the exercise recognition unit 130 determines a section on the time axis to which the input image belongs (step S230).

Next, the score calculation unit 160 determines whether or not to calculate an effectiveness score for the input image (step S240). When it is determined to calculate the effectiveness score in step S140, the score calculation unit 160 compares the exercise of the person reflected in the input image with the exercise model generated by the model generation unit 255, and calculates the effectiveness score on the basis of a difference between them (step S250).

Next, the object generation unit 270 generates a virtual object that exaggerates motion of a target region according to the greatness of the effectiveness score calculated by the score calculation unit 160 (step S260). Also, the object generation unit 270 determines whether or not it is necessary to display the exercise model according to a setting (step S270), and also generates a virtual object that represents the exercise model when it is necessary to display the exercise model (step S280).

The display control unit 180 superimposes the virtual objects generated by the object generation unit 270 on the input image, and causes the display unit 110 to display the virtual objects (step S290).

3-3. Summary of Second Embodiment

Thus far, the second embodiment of the technology related to the present disclosure has been described. In this embodiment, an effectiveness score that represents effectiveness of exercise of a person reflected in an input image is calculated, and a virtual object that represents the greatness of the calculated effectiveness score is superimposed on the input image. Accordingly, it is possible to present feedback about effectiveness of the exercise to a user in a visualized form. Also, since the effectiveness score is calculated on the basis of a difference between an exercise model regarded as an objective and the exercise, the user's motivation to achieve the objective can be enhanced.

Also, in this embodiment, an exercise model appropriate for an exerciser is generated on the basis of an objective and a record of exercise. Accordingly, when exercise management is necessary for each individual, an effectiveness score that is more appropriate for an exercise situation is calculated, and each exercise can be effectively supported.

Also, in this embodiment, motion of a target region of exercise is exaggeratively represented by a virtual object according to the greatness of an effectiveness score. In other words, when a result of daily exercise, such as a rehabilitation exercise and the like, is shown to be very little as actual motion, the result is presented to a user in an emphasized form. Accordingly, the user's motivation for the exercise can be further enhanced.

4. Third Embodiment

In a third embodiment described in this chapter, an expected change in the appearance of an exerciser is presented to a user. An image processing device 300 related to this embodiment handles, for example, exercises for training. However, this embodiment is not limited to this example, and can also be applied to other types of exercises.

4-1. Functional Configuration

Figure 14:
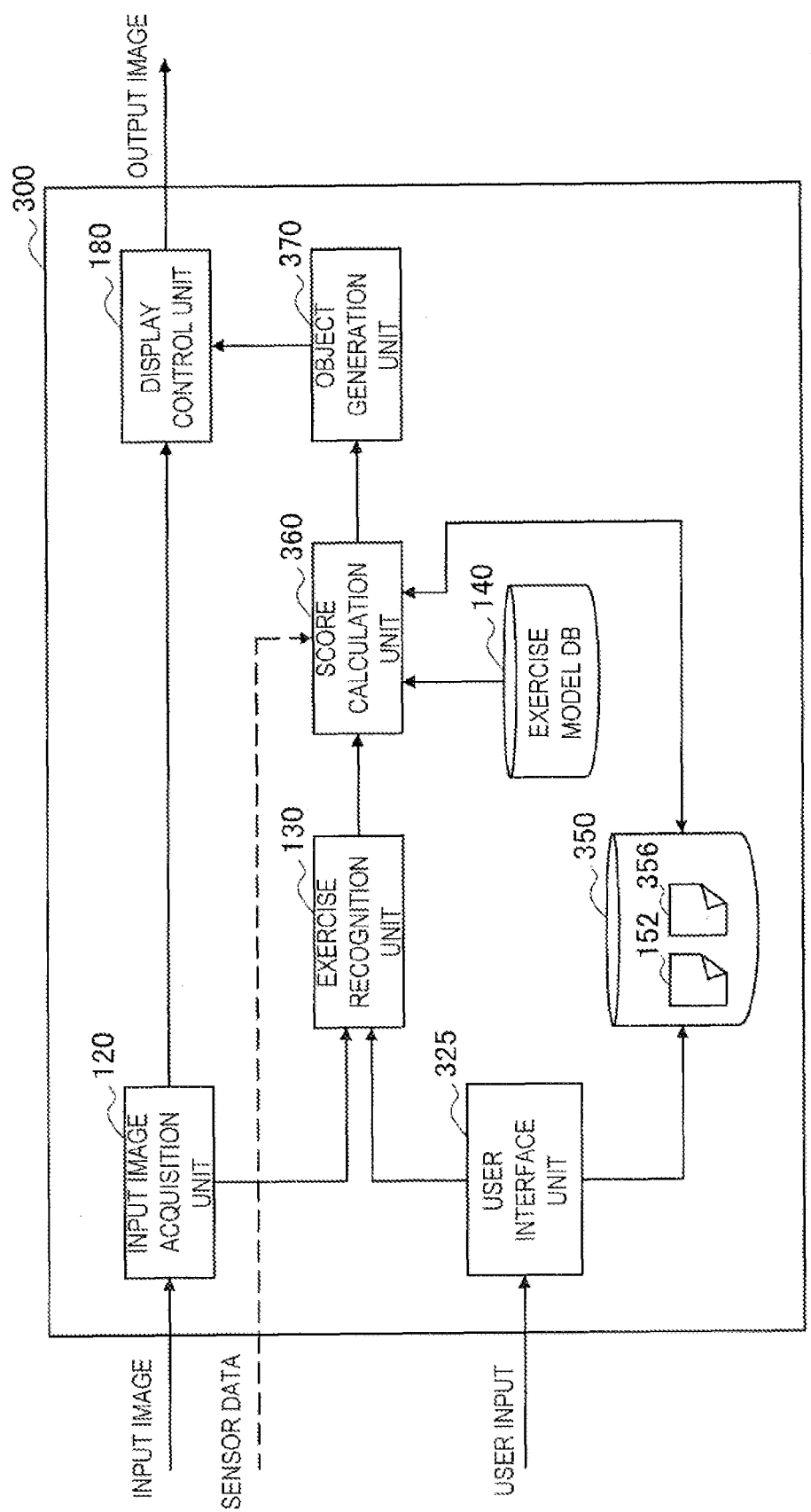
FIG. 14 is a block diagram showing an example of a configuration of logical functions of an image processing device related to a third embodiment.

A hardware configuration of the image processing device 300 may be equivalent to the hardware configuration of the image processing device 100 exemplified in FIG. 2. FIG. 14 is a block diagram showing an example of a configuration of logical functions implemented in the image processing device 300. Referring to FIG. 14, the image processing device 300 includes an input image acquisition unit 120, a user interface unit 325, an exercise recognition unit 130, an exercise model DB 140, a user DB 350, a score calculation unit 360, an object generation unit 370, and a display control unit 180.

(1) User Interface Unit

The user interface unit 325 provides a user with a user interface that receives an input of living history data used for conversion from an effectiveness score, which will be described later, to a body type score. The living history data can include, for example, the amount that the user eats, the amount of exercise while the user is out, the amount of sleep, and the like that are input at predetermined time periods (one day, one week, or the like). These pieces of data may be input through the input unit 106 of the image processing device 300, or input to the terminal device 10 as exemplified in FIG. 1B and received through the communication unit 112.

(2) User DB

The user DB 350 is a DB in which a variety of data prepared for each individual user is accumulated. The user DB 350 stores the attribute data 152 which has been described in connection with the first embodiment. Further, in this embodiment, the user DB 350 stores aforementioned living history data 356 that is acquired through the user interface unit 325.

Figures 15, 16:
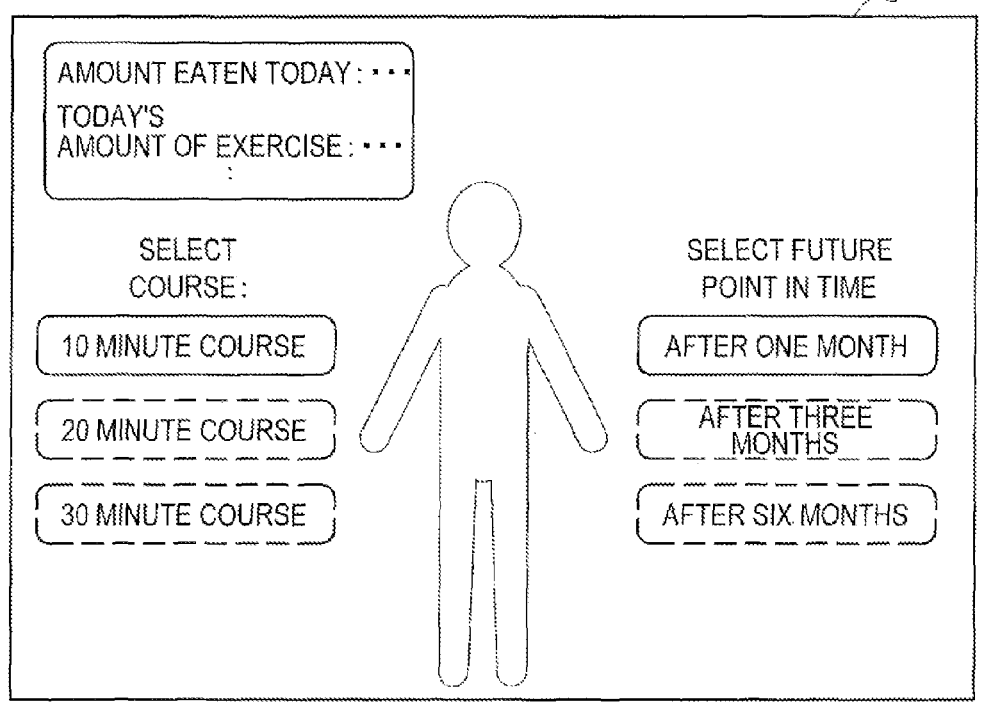
FIG. 15 is an explanatory diagram showing an example of living history data.
FIG. 16 is an explanatory diagram showing an example of an image displayed upon the start of exercise in the third embodiment.

Referring to FIG. 15, the living history data 356 is shown as an example that is stored in the user DB 350. The living history data 356 has five data categories referred to as "Person ID," "Date," "Amount Eaten," "Amount of Exercise," and "Amount of Sleep." A "Person ID" is an identifier for uniquely identifying an exerciser. A "Date" denotes a date that is related to living history denoted by the corresponding record. An "Amount Eaten" denotes the amount that a person identified by the person ID has eaten in the corresponding period. An "Amount of Exercise" denotes the amount of exercise that the person has performed while he/she is out, and the like in the corresponding period. An "Amount of Sleep" denotes the amount of time for which the person has slept in the corresponding period.

(3) Score Calculation Unit

The score calculation unit 360 calculates a score that represents effectiveness of exercise recognized by the exercise recognition unit 130, like the score calculation unit 160 related to the first embodiment. More specifically, when exercise is recognized by the exercise recognition unit 130, the score calculation unit 360 calculates an effectiveness score on the basis of a difference between the recognized exercise and an exercise model according to any of the methods described with reference to FIG. 6A to FIG. 6D (or another method). Further, in this embodiment, the score calculation unit 360 acquires the living history data 356 of the exerciser from the user DB 350, and converts the effectiveness score into a body type score using the acquired data. Herein, as an example, the greater the body type score, the more the person weighs. The body type score is calculated according to at least a reference C1 below. Also, one or more of a reference C2 to a reference C4 may be combined with the reference C1.

Reference C1: the greater the effectiveness score, the less the body type score

Reference C2: the more the amount eaten in a predetermined period, the greater the body type score Reference C3: the more the amount of exercise in a predetermined period, the less the body type score Reference C4: the more the amount of sleep in a predetermined period, the greater the body type score The score calculation unit 360 calculates a body type score for every section in this way, and outputs the calculated body type scores to the object generation unit 370.

(4) Object Generation Unit

The object generation unit 370 generates a virtual object that represents the greatness of the effectiveness score. In this embodiment, the object generation unit 370 generates the virtual object to be superimposed on an input image practically according to a value of the body type score converted from the effectiveness score. The virtual object generated by the object generation unit 370 may be an object that represents the future appearance of a target region for a case in which the currently performed exercise is continuously performed.

FIG. 16 is an explanatory diagram showing an example of an image displayed upon the start of exercise in the third embodiment. FIG. 16 shows an image Im6 of a user interface for causing a user to select a course classified according to the length of exercise time and a future point in time. Upon the start of exercise, the user selects both a course and a future point in time. Here, the future point in time selected by the user becomes a temporal reference when the object generation unit 370 estimates the future appearance of a target region.

Figure 17:
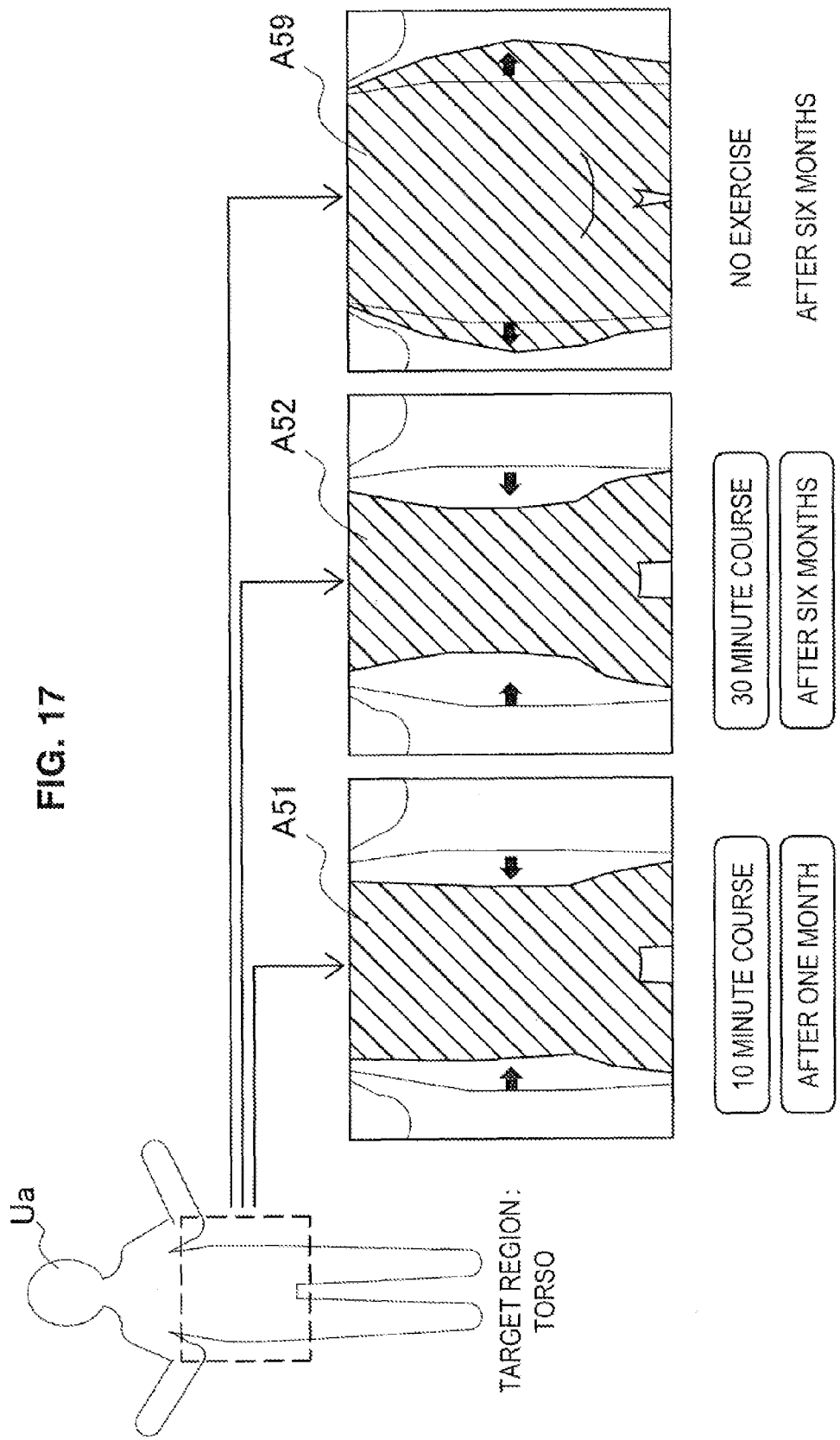
FIG. 17 is an explanatory diagram illustrating an example of an object generation process by an object generation unit exemplified in FIG. 14.

FIG. 17 is an explanatory diagram illustrating an example of an object generation process by the object generation unit 370. On the upper left side of FIG. 17, a silhouette of a user Ua who is an exerciser is shown. Here, a target region of exercise is a torso. The object generation unit 370 estimates the appearance of the target region at a selected future point in time according to the length of exercise time corresponding to a course selected by the user, the length of time that elapses until the future point in time, and a body type score calculated by the score calculation unit 360 during the exercise. For example, the appearance of the target region can be estimated for a case in which the exercise of the same course is continuously performed once a day until the future point in time. Here, it is important to change the estimated body type in a visualized form, and the accuracy of the estimation is not important. Thus, the estimation may not be precise. A virtual object A51 shown in FIG. 17 is an object that represents a slightly slenderized torso of the user Ua and can be generated when "10 minute course" and "After one month" are selected. A virtual object A52 is an object that represents a further slenderized torso of the user Ua and can be generated when "30 minute course" and "After six months" are selected. Also, the object generation unit 370 may generate an object that represents the future appearance of the target region for a case in which no exercise is performed. A virtual object A59 shown in FIG. 17 is an object that represents a fat torso of the user Ua on the assumption that no exercise is performed.

Figure 18:
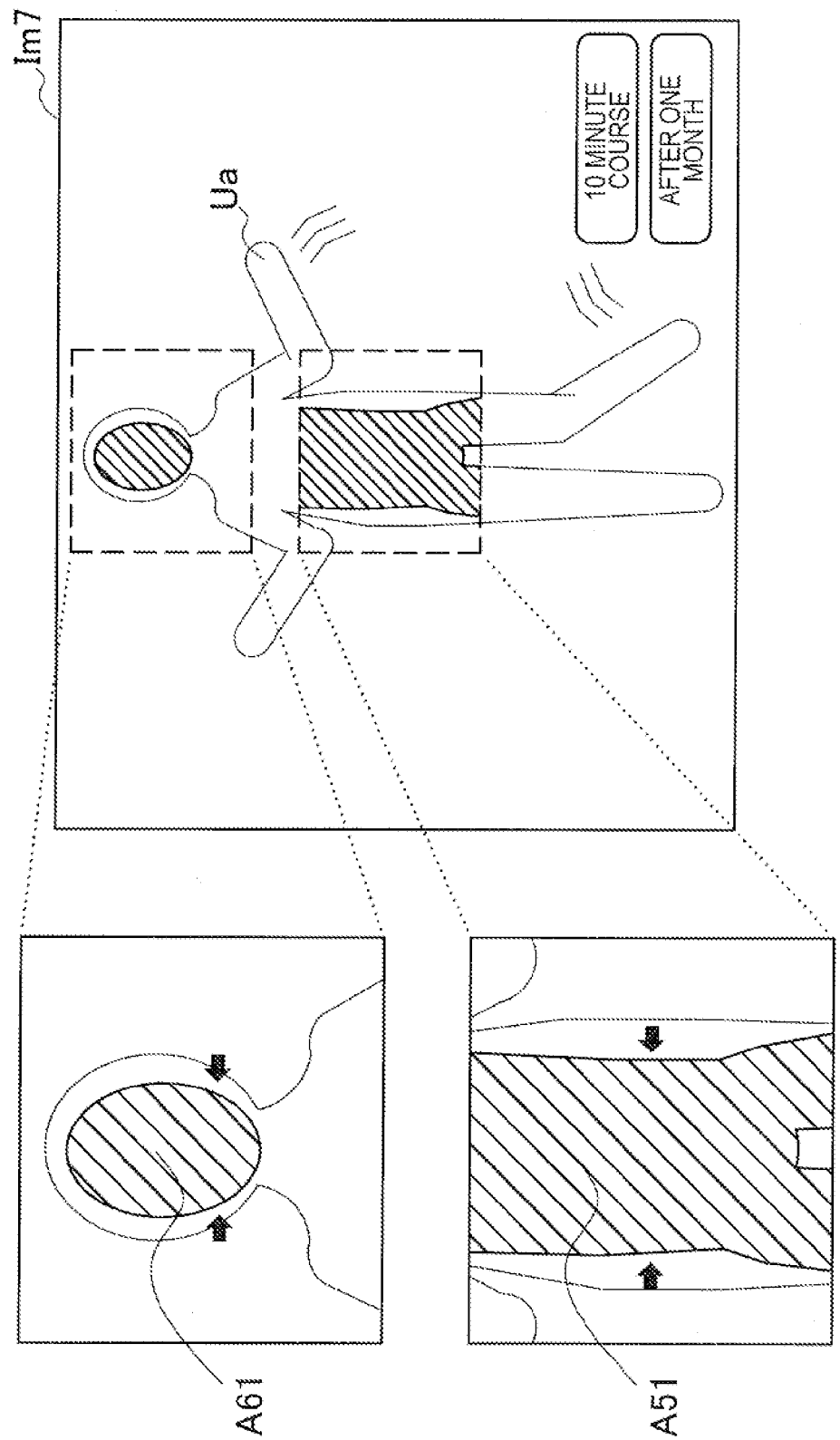
FIG. 18 is an explanatory diagram illustrating an example of a virtual object displayed in the third embodiment.

FIG. 18 is an explanatory diagram illustrating an example of a virtual object displayed in this embodiment. In FIG. 18, an output image Im7 is shown as an example that can be displayed by the display unit 110 of the image processing device 300, and the output image Im7 shows the user Ua who is performing a shape-up exercise. Upon the start of the shape-up exercise, "10 minute course" and "After one month" have been selected.

In the output image Im7, the virtual object A51 exemplified in FIG. 17 is superimposed on the torso of the user Ua. Also, a virtual object A61 is superimposed on the head of the user Ua. The respective virtual objects A51 and A61 represent target regions of the user Ua that become slightly slenderer at a selected future point in time. Although not shown in the drawing, a virtual object that represents an appearance estimated on the assumption that no exercise is performed (the virtual object A59 exemplified in FIG. 17, and the like) may additionally be superimposed on the vicinity of the user Ua. These virtual objects are shown to the user, and the user thereby becomes aware of an expected result of the exercise, so that the user can be motivated to continue the shape-up exercise.

4-2. Flow of Process

Figure 19:
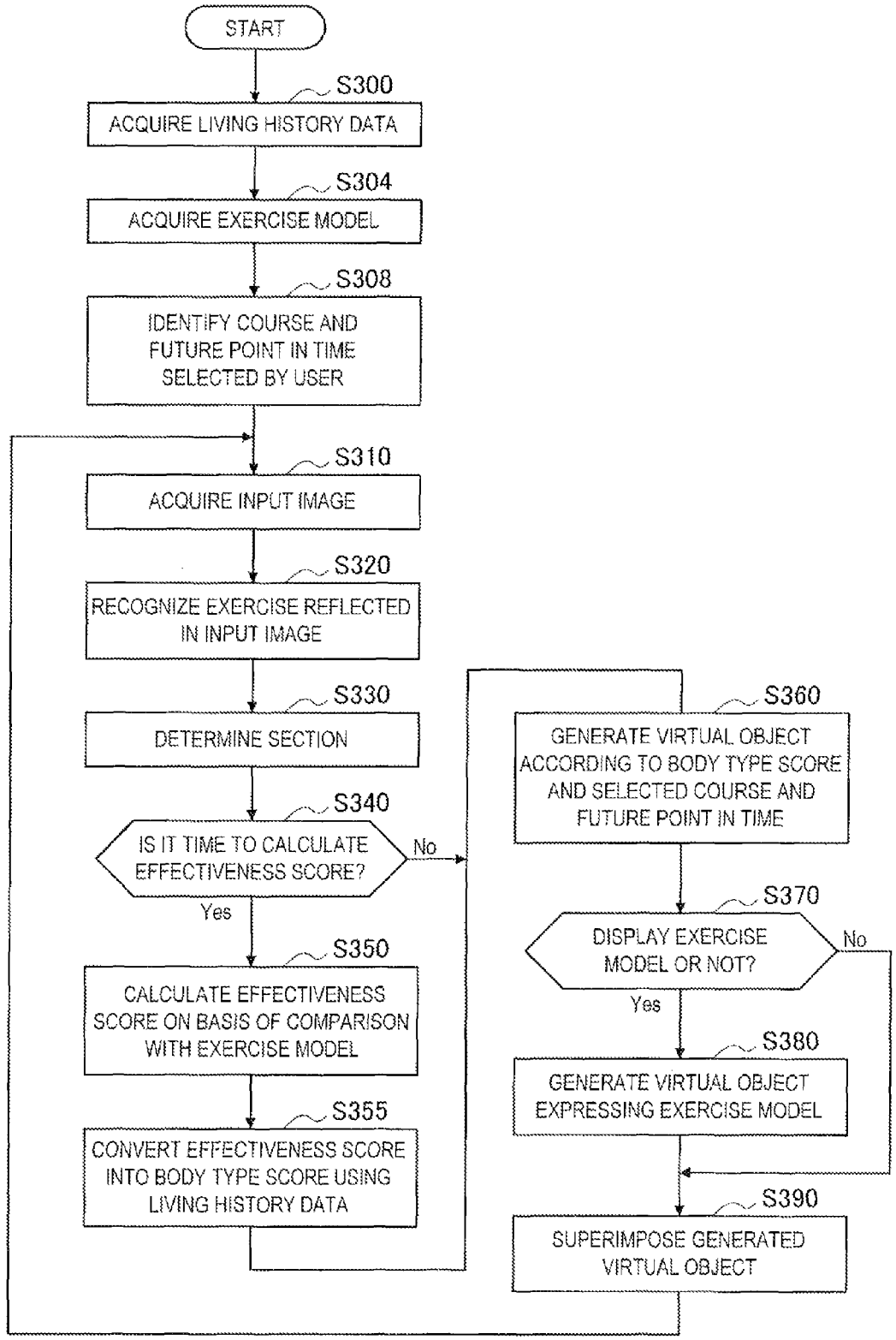
FIG. 19 is a flowchart showing an example of image processing flow related to the third embodiment.

FIG. 19 is a flowchart showing an example of flow of image processing by the image processing device 300 related to this embodiment.

Referring to FIG. 19, around the start of exercise, the score calculation unit 360 acquires the living history data 356 accumulated in the user DB 350 (step S300). Also, the score calculation unit 360 acquires any of exercise models stored by the exercise model DB 140 (step S304). The object generation unit 370 identifies an exercise course and a future point in time that have been selected by a user through the user interface unit 325 (step S308). A process of the following steps S310 to S390 is repeated for each of a series of input images.

First, the input image acquisition unit 120 acquires a captured image generated by the imaging unit 102 as an input image (step S310).

Next, the exercise recognition unit 130 recognizes the exercise of a person reflected in the input image from the input image acquisition unit 120 (step S320). Then, the exercise recognition unit 130 determines a section on the time axis to which the input image belongs (step S330).

Next, the score calculation unit 360 determines whether or not to calculate a score for the input image (step S340). When it is determined to calculate the score in step S340, the score calculation unit 360 compares the exercise of the person reflected in the input image with the exercise model, and calculates the effectiveness score on the basis of a difference between them (step S350). Also, the score calculation unit 360 converts the effectiveness score into a body type score using the living history data 356 (step S355).

Next, the object generation unit 370 generates a virtual object that represents the future appearance of a target region according to the body type score input from the score calculation unit 360 and the course and the future point in time selected by the user (step S360). Also, the object generation unit 370 determines whether or not it is necessary to display the exercise model according to a setting (step S370), and also generates a virtual object that represents the exercise model when it is necessary to display the exercise model (step S380).

The display control unit 180 superimposes the virtual objects generated by the object generation unit 370 on the input image, and causes the display unit 110 to display the virtual objects (step S390).

4-3. Summary of Third Embodiment

Thus far, the third embodiment of the technology related to the present disclosure has been described. In this embodiment, an effectiveness score that denotes effectiveness of exercise of a person reflected in an input image is converted into a body type score, and a virtual object that represents the greatness of the body type score is superimposed on the input image. Accordingly, it is possible to present feedback about effectiveness of the exercise to a user in a visualized form which is referred to as a virtual body type of the user.

Also, in this embodiment, the virtual object that is superimposed on the input image exaggeratively represents a change in the appearance of a target region of the exercise according to the greatness of the body type score. Also, the future appearance of the target region estimated for a case in which the exercise is continuously performed is presented to the user. Accordingly, the user can be clearly aware of results of the exercise expected for the future, and can be motivated to continue the exercise.

Thus far, the three embodiments related to the present disclosure have been described in detail. A variety of characteristics of these embodiments may be combined in any form. For example, in the application of the first embodiment and the third embodiment, an exercise model appropriate for an exerciser may be generated on the basis of an objective and a record of exercise. Also, for example, in the application of the first embodiment and the second embodiment, an effectiveness score may be calculated by calculating and using living history data. In addition, according to a variety of exercise situations, an effectiveness score may be modified somehow or converted into another type of score.

The series of control processing by respective devices described in this specification may be implemented using any of software, hardware, and a combination of software and hardware. A program constituting the software is contained in advance in, for example, a storage medium installed in or outside each device. Upon execution, each program is read by, for example, a Random Access Memory (RAM), and executed by a processor such as a Central Processing Unit (CPU) or the like.

Also, some of logical functions of each device may be installed on a device that is present in a cloud computing environment instead of being installed on the corresponding device. In this case, information that is exchanged between logical functions can be transmitted or received between the devices through the communication unit 112 exemplified in FIG. 2.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An image processing device including:
a recognition unit that recognizes exercise of a person reflected in an input image; and
a display control unit that superimposes on the input image a virtual object varying according to effectiveness of the exercise recognized by the recognition unit.

(2) The image processing device according to (1), further including:
a score calculation unit that calculates a score denoting the effectiveness of the exercise recognized by the recognition unit,
wherein the display control unit superimposes on the input image the virtual object representing greatness of the score calculated by the score calculation unit.

(3) The image processing device according to (2),
wherein the score calculation unit calculates the score based on a difference between an exercise model regarded as an objective and the exercise.

(4) The image processing device according to (3),
wherein the exercise model is data obtained by modeling exercise of a person who is a teacher in advance.

(5) The image processing device according to (3), further including:

a model generation unit that generates the exercise model based on an objective and a record of the exercise of the person.

(6) The image processing device according to any one of (2) to (5), wherein the virtual object is an object emphasizing a target region of the exercise.

(7) The image processing device according to (6), wherein the virtual object exaggeratively represents a change in an appearance of the target region according to the greatness of the score.

(8) The image processing device according to (7), wherein the virtual object represents a future appearance of the target region for a case in which the exercise is continuously performed.

(9) The image processing device according to (6), wherein the virtual object exaggeratively represents motion of the target region according to the greatness of the score.

(10) The image processing device according to any one of (6) to (9), wherein the display control unit superimposes the virtual object on a position in the input image at which the target region is reflected.

(11) The image processing device according to any one of (2) to (9), wherein the display control unit superimposes the virtual object on a vicinity of the person in the input image.

(12) The image processing device according to any one of (2) to (11), wherein the score calculation unit calculates the score by additionally using sensor data supplementarily denoting the effectiveness of the exercise.

(13) The image processing device according to any one of (2) to (11), wherein the score calculation unit calculates the score by additionally using living history data representing a living history of the person.

(14) The image processing device according to any one of (2) to (13), wherein at least one of the recognition unit, the score calculation unit, and the display control unit is implemented by a device present in a cloud computing environment instead of the image processing device.

(15) An image processing method including:

recognizing exercise of a person reflected in an input image; and superimposing on the input image a virtual object varying according to effectiveness of the recognized exercise.

(16) A program for causing a computer controlling an image processing device to function as:

a recognition unit that recognizes exercise of a person reflected in an input image; and a display control unit that superimposes on the input image a virtual object varying according to effectiveness of the exercise recognized by the recognition unit.

What is claimed is:

1. An image processing device comprising:
 a processor device that:
  recognizes exercise of a person reflected in an input image, by determining a section on a time axis of frames included in a series of input images to which the input image corresponds;
  determines, for each section of a plurality of sections on the time axis corresponding to a recognized exercise, whether to calculate a score denoting effectiveness of the exercise recognized based on whether or not at least one frame thereof includes a predetermined pose such that (i) a respective score is to be calculated when the at least one frame thereof includes the predetermined pose and (ii) the respective score is not to be calculated when the at least one frame thereof does not include the predetermined pose;
  calculates the score when a determination result indicates that the score is to be calculated; and
  superimposes on the input image a virtual object varying according to the effectiveness of the exercise recognized.

2. The image processing device according to claim 1, wherein the processor device superimposes on the input image the virtual object representing greatness of the score calculated.

3. The image processing device according to claim 2, wherein the processor device calculates the score based on a difference between an exercise model regarded as an objective and the exercise.

4. The image processing device according to claim 3, wherein the exercise model is data obtained by modeling exercise of a person who is a teacher in advance.

5. The image processing device according to claim 3, wherein the processor device generates the exercise model based on an objective and a record of the exercise of the person.

6. The image processing device according to claim 2, wherein the virtual object is an object emphasizing a target region of the exercise.

7. The image processing device according to claim 6, wherein the virtual object exaggeratively represents a change in an appearance of the target region according to the greatness of the score.

8. The image processing device according to claim 7, wherein the virtual object represents a future appearance of the target region for a case in which the exercise is continuously performed.

9. The image processing device according to claim 6, wherein the virtual object exaggeratively represents motion of the target region according to the greatness of the score.

10. The image processing device according to claim 6, wherein the processor device superimposes the virtual object on a position in the input image at which the target region is reflected.

11. The image processing device according to claim 2, wherein the processor device superimposes the virtual object on a vicinity of the person in the input image.

12. The image processing device according to claim 2, wherein the processor device calculates the score by additionally using sensor data supplementarily denoting the effectiveness of the exercise.

13. The image processing device according to claim 2, wherein the processor device calculates the score by additionally using living history data representing a living history of the person.

14. The image processing device according to claim 2, wherein at least a portion of the processor device is implemented by a device present in a cloud computing environment instead of the image processing device.

15. The image processing device according to claim 1, in which the score is calculated by the processor device by use of a plurality of calculation methods, each calculation method being different from each other.

16. The image processing device according to claim 1, in which a result from each said calculation method is weighted and added together to obtain the score.

17. An image processing method comprising:
- recognizing exercise of a person reflected in an input image, by determining a section on a time axis of frames included in a series of input images to which the input image corresponds;
- determining, for each section of a plurality of sections on the time axis corresponding to a recognized exercise, whether to calculate a score denoting effectiveness of the exercise recognized based on whether or not at least one frame thereof includes a predetermined pose such that (i) a respective score is to be calculated when the at least one frame thereof includes the predetermined pose and (ii) the respective score is not to be calculated when the at least one frame thereof does not include the predetermined pose;
- calculating the score when a determination result indicates that the score is to be calculated; and
- superimposing on the input image a virtual object varying according to the effectiveness of the recognized exercise.

18. A non-transitory recording medium on which a program is recorded for causing a computer controlling an image processing device to function as:
- a recognition unit that recognizes exercise of a person reflected in an input image, by determining a section on a time axis of frames included in a series of input images to which the input image corresponds;
- a score calculation unit that determines, for each section of a plurality of sections on the time axis corresponding to a recognized exercise, whether to calculate a score denoting effectiveness of the exercise recognized based on whether or not at least one frame thereof includes a predetermined pose such that (i) a respective score is to be calculated when the at least one frame thereof includes the predetermined pose and (ii) the respective score is not to be calculated when the at least one frame thereof does not include the predetermined pose;
- a calculation unit to calculate the score when a determination result from the score calculation unit indicates that the score is to be calculated; and
- a display control unit that superimposes on the input image a virtual object varying according to the effectiveness of the exercise recognized by the recognition unit.

* * * * *